(12) United States Patent
Selim et al.

(10) Patent No.: US 12,406,413 B2
(45) Date of Patent: Sep. 2, 2025

(54) PREDICTIVE DATA ANALYSIS USING IMAGE REPRESENTATIONS OF GENOMIC DATA

(71) Applicant: Optum Services (Ireland) Limited, Dublin (IE)

(72) Inventors: Ahmed Selim, Dublin (IE); Paul J. Godden, London (GB); Michael Bridges, Dublin (IE)

(73) Assignee: Optum Services (Ireland) Limited, Dublin (IE)

( * ) Notice: Subject to any disclaimer, the term of this patent is extended or adjusted under 35 U.S.C. 154(b) by 934 days.

(21) Appl. No.: 17/473,064

(22) Filed: Sep. 13, 2021

(65) Prior Publication Data

US 2022/0358697 A1 Nov. 10, 2022

Related U.S. Application Data

(60) Provisional application No. 63/201,699, filed on May 10, 2021.

(51) Int. Cl.
*G06T 11/20* (2006.01)
*G06N 5/04* (2023.01)
(Continued)

(52) U.S. Cl.
CPC .............. *G06T 11/206* (2013.01); *G06N 5/04* (2013.01); *G06T 7/0012* (2013.01); *G16B 5/20* (2019.02);
(Continued)

(58) Field of Classification Search
None
See application file for complete search history.

(56) References Cited

U.S. PATENT DOCUMENTS 6,611,828 B1 8/2003 Koleszar et al.
9,898,578 B2 2/2018 Yakhini et al.
(Continued)

FOREIGN PATENT DOCUMENTS

KR 10-2215529 B1 2/2021
WO WO-2005056837 A2 * 6/2005 ............. A61K 31/22
(Continued)

OTHER PUBLICATIONS

"Genetic Data," Biobank UK, (7 pages), (online), [Retrieved from the Internet Oct. 27, 2021] <https://www.ukbiobank.ac.uk/enable-your-research/about-our-data/genetic-data>.
(Continued)

*Primary Examiner* — Tsung Yin Tsai
(74) *Attorney, Agent, or Firm* — ALSTON & BIRD LLP

(57) ABSTRACT

There is a need for more effective and efficient predictive data analysis solutions and/or more effective and efficient solutions for generating image representations of genetic variant data. In one example, embodiments comprise receiving an input feature, generating one or more image representations of the input feature, generating a tensor representation of the one or more image representations, generating a plurality of positional encoding maps, generating an image-based prediction based at least in part on the image representation, and performing one or more prediction-based actions based at least in part on the image-based prediction.

20 Claims, 24 Drawing Sheets

(51) Int. Cl.
  *G06T 7/00* (2017.01)
  *G16B 5/20* (2019.01)
  *G16B 45/00* (2019.01)
(52) U.S. Cl.
  CPC .... *G16B 45/00* (2019.02); *G06T 2207/20081* (2013.01); *G06T 2207/20084* (2013.01)

(56) References Cited

U.S. PATENT DOCUMENTS

| | | | |
|---|---|---|---|
| 10,769,162 B2 | 9/2020 | Rope et al. | |
| 2003/0190657 A1 | 10/2003 | White | |
| 2006/0147922 A1* | 7/2006 | Watts | C12Q 1/6886 435/6.14 |
| 2007/0003929 A1* | 1/2007 | Hayashizaki | C12Q 1/6827 435/6.15 |
| 2014/0160132 A1* | 6/2014 | Xing | G16B 45/00 345/440 |
| 2016/0048608 A1 | 2/2016 | Frieden et al. | |
| 2017/0098031 A1 | 4/2017 | OBrien et al. | |
| 2019/0214111 A1 | 7/2019 | Alberti et al. | |
| 2020/0051667 A1* | 2/2020 | Alberti | H03M 7/70 |
| 2021/0304841 A1* | 9/2021 | Renzi | G16B 50/30 |
| 2023/0274800 A1* | 8/2023 | Alberti | G16B 30/10 702/19 |

FOREIGN PATENT DOCUMENTS

| | | | | |
|---|---|---|---|---|
| WO | WO-2018068827 A1 * | 4/2018 | | G16B 20/20 |
| WO | WO-2019169452 A1 * | 9/2019 | | G06F 16/9024 |

OTHER PUBLICATIONS

"Google/DeepVariant," GitHub, (8 pages), (online), [Retrieved from the Internet Oct. 27, 2021] <URL:https://github.com/google/deepvariant>.

"Loss Of Heterozygosity—NCI Dictionary Of Genetic Terms," National Cancer Institute, (1 page), (online), [Retrieved from the Internet Oct. 27, 2021] <URL:https://www.cancer.gov/publications/dictionaries/genetics-dictionary/def/loss-of-heterozygosity>.

Badre, Adrien et al. "Deep Neural Network Improves The Estimation Of Polygenic Risk Scores For Breast Cancer," Journal of Human Genetics, vol. 66, No. 4, (20 pages), Oct. 2, 2020, DOI:10.1038/s10038-020-00832-7, PMID: 33009504.

Chai, Hua et al. "Integrating Multi-Omics Data With Deep Learning For Predicting Cancer Prognosis," bioRxiv preprint, pp. 1-7, Oct. 17, 2019, DOI: 10.1101/807214.

Chaudhary, Kumardeep et al. "Deep Learning Based Multi-Omics Integration Robustly Predicts Survival In Liver Cancer," Clinical Cancer Resarch, vol. 24, No. 6, pp. 1248-1259, Mar. 15, 2018, DOI: 10.1158/1078-0432.CCR-17-0853.

Huang, Zhi et al. "SALMON: Survival Analysis Learning With Multi-Omics Neural Networks on Breast Cancer," Frontiers In Genetics, vol. 10, Article 166, pp. 1-13, Mar. 8, 2019, DOI: 10.3389/fgene.2019.00166.

Ma, Tianle et al. "Integrate Multi-Omics Data With Biological Interaction Networks Using Multi-View Factorization AutoEncoder (MAE)," BMC Genomics, vol. 20, Supplement 11:944, pp. 1-11, Dec. 20, 2019, DOI: 10.1186/s12864-019-6285-x.

Neto, Elias Chaibub et al. "Causal Graphical Models In Systems Genetics—A Unified Framework For Joint Inference Of Causal Network and Genetic Architecture For Correlated Phenotypes," The Annals of Applied Statistics, vol. 4, No. 1, pp. 320-339, Mar. 1, 2010.

Nguyen, Nam D. et al. "Multiview Learning For Understanding Functional Multiomics," PLoS Computational Biology, vol. 16, No. 4:e1007677, pp. 1-26, Apr. 2, 2020, DOI: 10.1371/journal.pcbi.1007677.

Nichols, Caitlin A. et al. "Loss Of Heterozygosity of Essential Genes Represents A Widespread Class Of Potential Cancer Vulnerabilities," Nature Communications, vol. 11, No. 2517, pp. 1-14, May 20, 2020, DOI: 10.1038/s41467-020-16399-y.

Perry, Ronan et al. "mvlearn: Multiview Machine Learning In Python," arXiv preprint arXiv:2005.11890v4, May 25, 2021, (5 pages).

Schreiber, Jacob et al. "Multi-Scale Deep Tensor Factorization Learns A Latent Representation Of The Human Epigenome," bioRxiv preprint, pp. 1-19, Apr. 11, 2019, DOI: 10.1101/364976.

Sharifi-Noghabi, Hossein et al. "MOLI: Multi-Omics Late Integration With Deep Neural Networks For Drug Response Prediction," Bioinformatics, vol. 35, Issue 14, pp. i501-i509, Jul. 5, 2019, DOI: 10.1093/bioinformatics/btz318.

Torada, Luis et al. "ImaGene: A Convolutional Neural Network to Quantify Natural Selection From Genomic Data," BMC Bioinformatics, vol. 20, Supplement 9:337, pp. 1-12, Nov. 22, 2019, DOI: 10.1186/s12859-019-2927-x.

Van Riet, Job et al. "SNPitty: An Intuitive Web Application for Interactive B-Allele Frequency and Copy Number Visualization of Next-Generation Sequencing Data," The Journal of Molecular Diagnostics, vol. 20, No. 2, pp. 166-176, Mar. 2018, DOI: 10.1016/j.jmoldx.2017.11.011.

Vdauwera, Geraldine. "Best Practices For Variant Discovery In DNAseq," Github Broad Institute/gatk-dics, (4 pages), (article, online), [Retrieved from the Internet Oct. 27, 2021] <URL: https://github.com/broadinstitute/gatk-docs/blob/master/gatk3-methods-and-algorithms/Best_Practices_for_Variant_Discovery_in_DNAseq.md>.

* cited by examiner

500

Allele 1

| rsID | DNA Nucleotide | MAF |
|---|---|---|
| rs1 | A | 0.2 |
| rs2 | A | 0.5 |
| rs3 | G | 0.3 |
| rs4 | C | 0.2 |
| rs5 | T | 0.5 |
| rs6 | T | 0 |
| rs7 | G | 0.3 |
| rs8 | A | 0.4 |
| rs9 | A | 0.3 |

| rsID | Minor Allele | Dominant Allele | Dominant Allele String | Minor Allele String |
|------|--------------|-----------------|------------------------|---------------------|
| rs1  | A            | G               | GTAT                   | ACCC                |
| rs2  | C            | T               |                        |                     |
| rs3  | C            | A               |                        |                     |
| rs4  | C            | T               |                        |                     |

PREDICTIVE DATA ANALYSIS USING IMAGE REPRESENTATIONS OF GENOMIC DATA

CROSS-REFERENCES TO RELATED APPLICATION(S)

The present application claims priority to U.S. Provisional Patent Application No. 63/201,699 (filed May 10, 2021), which is incorporated herein by reference in its entirety.

BACKGROUND

Various embodiments of the present invention address technical challenges related to performing predictive data analysis in a computationally efficient and predictively reliable manner. Existing predictive data analysis systems are ill-suited to efficiently and reliably perform predictive data analysis in various domains, such as domains that are associated with high-dimensional feature spaces.

BRIEF SUMMARY

In general, embodiments of the present invention provide methods, apparatuses, systems, computing devices, computing entities, and/or the like dynamically generating an image-based prediction based at least in part on an input feature.

In accordance with one aspect, a method includes: receiving, using one or more processors, an input feature, wherein the input feature comprises one or more feature values, wherein each feature value of the one or more feature values corresponds to a genetic variant identifier, and wherein each feature value is associated with an input feature type designation of a plurality of input feature type designations; generating, using the one or more processors, one or more image representations of the input feature, wherein: (i) an image representation count of the one or more image representations is based at least in part on the plurality of input feature type designations (ii) each image representation of the one or more image representations comprises a plurality of image regions, (iii) each image region for an image representation corresponds to a genetic variant identifier, and (iv) generating each of the one or more image representations associated with a character category is performed based at least in part on the one or more feature values of the input feature having the input feature type designation; generating, using the one or more processors, a tensor representation of the one or more image representations of the input feature; generating, using the one or more processors, a plurality of positional encoding maps, wherein: (i) each positional encoding map of the one or more positional encoding maps comprises a plurality of positional encoding map regions, (ii) each positional encoding map region for a positional encoding map corresponds to a genetic variant identifier, (iii) each genetic variant identifier is associated with a positional encoding map region set comprising each positional encoding map region associated with the genetic variant identifier across the plurality of positional encoding maps, and (iv) each positional encoding map region set for a genetic variant identifier represents a the genetic variant identifier; generating, using the one or more processors, an image-based prediction based at least in part on the tensor representation of the one or more image representations of the input feature and the one or more positional encoding maps; and performing, using the one or more processors, one or more prediction-based actions based at least in part on the image-based prediction.

In accordance with another aspect, an apparatus comprising at least one processor and at least one memory including program code, the at least one memory and the program code configured to, with the processor, cause the apparatus to at least: receive an input feature, wherein the input feature comprises one or more feature values, wherein each feature value of the one or more feature values corresponds to a genetic variant identifier, and wherein each feature value is associated with an input feature type designation of a plurality of input feature type designations; generate one or more image representations of the input feature, wherein: (i) an image representation count of the one or more image representations is based at least in part on the plurality of input feature type designations (ii) each image representation of the one or more image representations comprises a plurality of image regions, (iii) each image region for an image representation corresponds to a genetic variant identifier, and (iv) generating each of the one or more image representations associated with a character category is performed based at least in part on the one or more feature values of the input feature having the input feature type designation; generate a tensor representation of the one or more image representations of the input feature; generate a plurality of positional encoding maps, wherein: (i) each positional encoding map of the one or more positional encoding maps comprises a plurality of positional encoding map regions, (ii) each positional encoding map region for a positional encoding map corresponds to a genetic variant identifier, (iii) each genetic variant identifier is associated with a positional encoding map region set comprising each positional encoding map region associated with the genetic variant identifier across the plurality of positional encoding maps, and (iv) each positional encoding map region set for a genetic variant identifier represents a the genetic variant identifier; generate an image-based prediction based at least in part on the tensor representation of the one or more image representations of the input feature and the one or more positional encoding maps; and perform one or more prediction-based actions based at least in part on the image-based prediction.

In accordance with yet another aspect, a computer program product computer program comprising at least one non-transitory computer-readable storage medium having computer-readable program code portions stored therein, the computer-readable program code portions configured to: receive an input feature, wherein the input feature comprises one or more feature values, wherein each feature value of the one or more feature values corresponds to a genetic variant identifier, and wherein each feature value is associated with an input feature type designation of a plurality of input feature type designations; generate one or more image representations of the input feature, wherein: (i) an image representation count of the one or more image representations is based at least in part on the plurality of input feature type designations (ii) each image representation of the one or more image representations comprises a plurality of image regions, (iii) each image region for an image representation corresponds to a genetic variant identifier, and (iv) generating each of the one or more image representations associated with a character category is performed based at least in part on the one or more feature values of the input feature having the input feature type designation; generate a tensor representation of the one or more image representations of the input feature; generate a plurality of positional encoding maps, wherein: (i) each positional encoding map of the one or more positional encoding maps comprises a plurality of positional encoding map regions, (ii) each positional encoding map region for a positional encoding map corresponds to a genetic variant identifier, (iii) each genetic variant identifier is associated with a positional encoding map region set comprising each positional encoding map region associated with the genetic variant identifier across the plurality of positional encoding maps, and (iv) each positional encoding map region set for an genetic variant identifier represents a the genetic variant identifier; generate an image-based prediction based at least in part on the tensor representation of the one or more image representations of the input feature and the one or more positional encoding maps; and perform one or more prediction-based actions based at least in part on the image-based prediction.

BRIEF DESCRIPTION OF THE DRAWINGS

Figure 1:
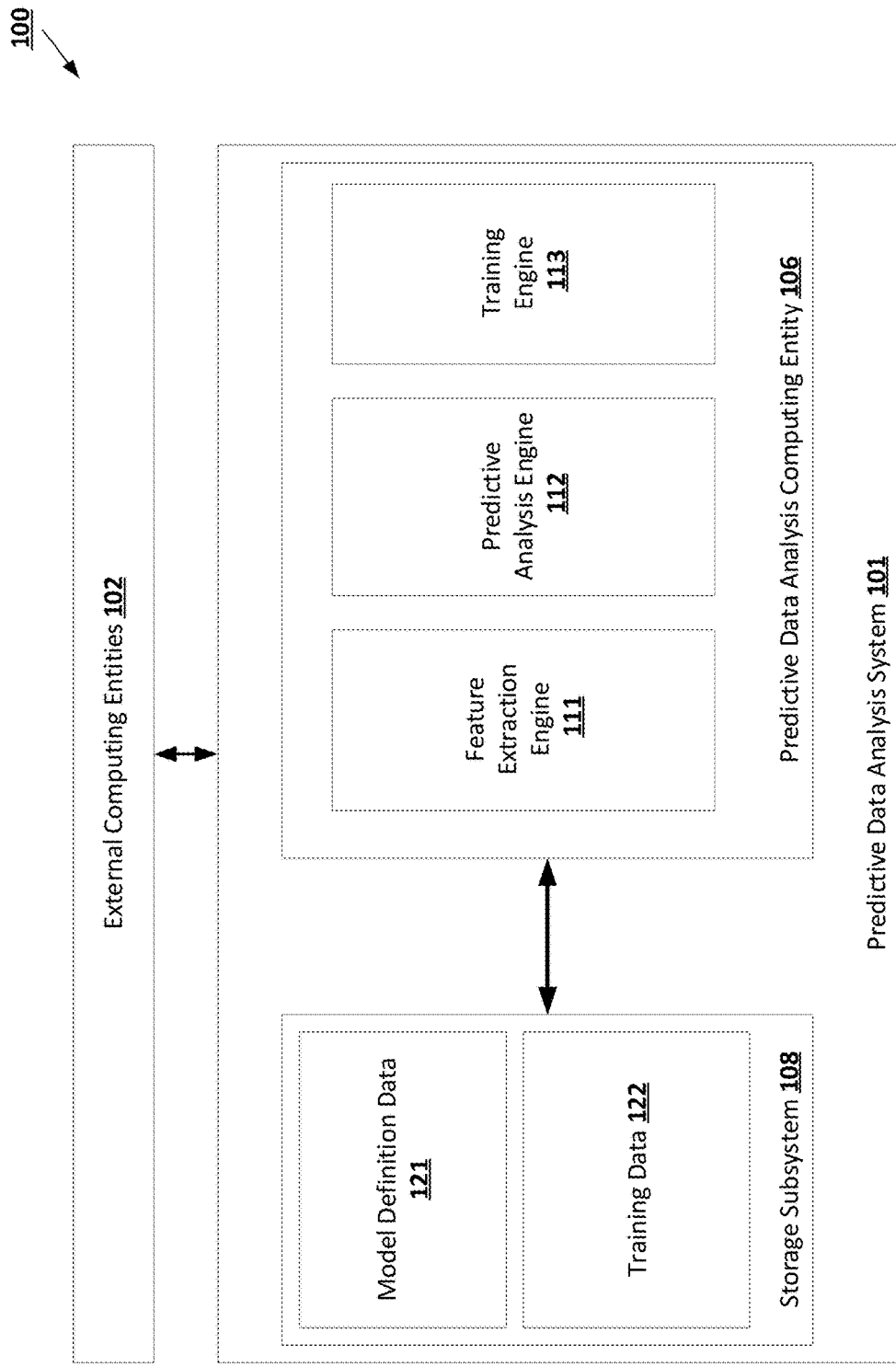
Figure 2:
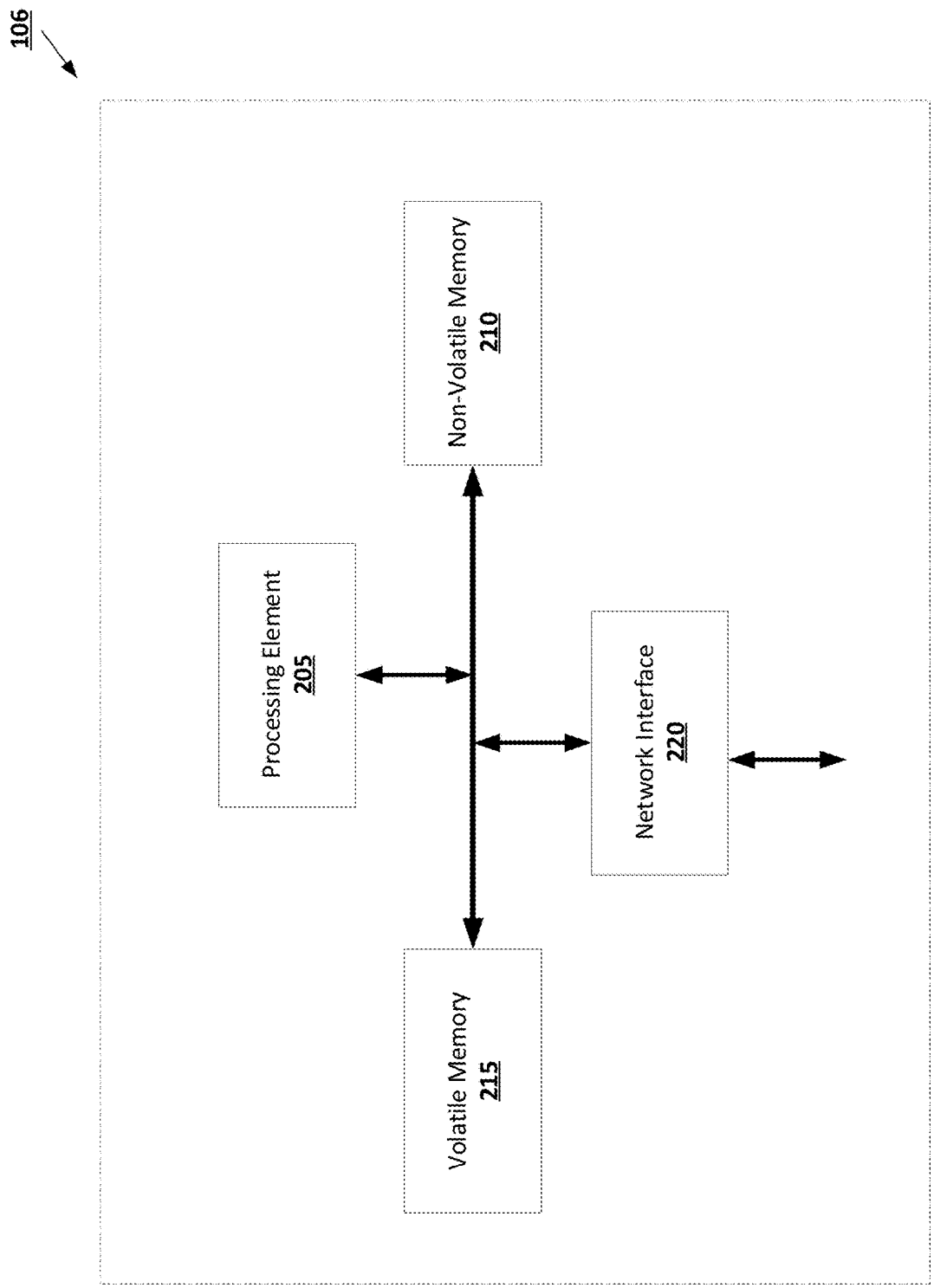
Figure 3:
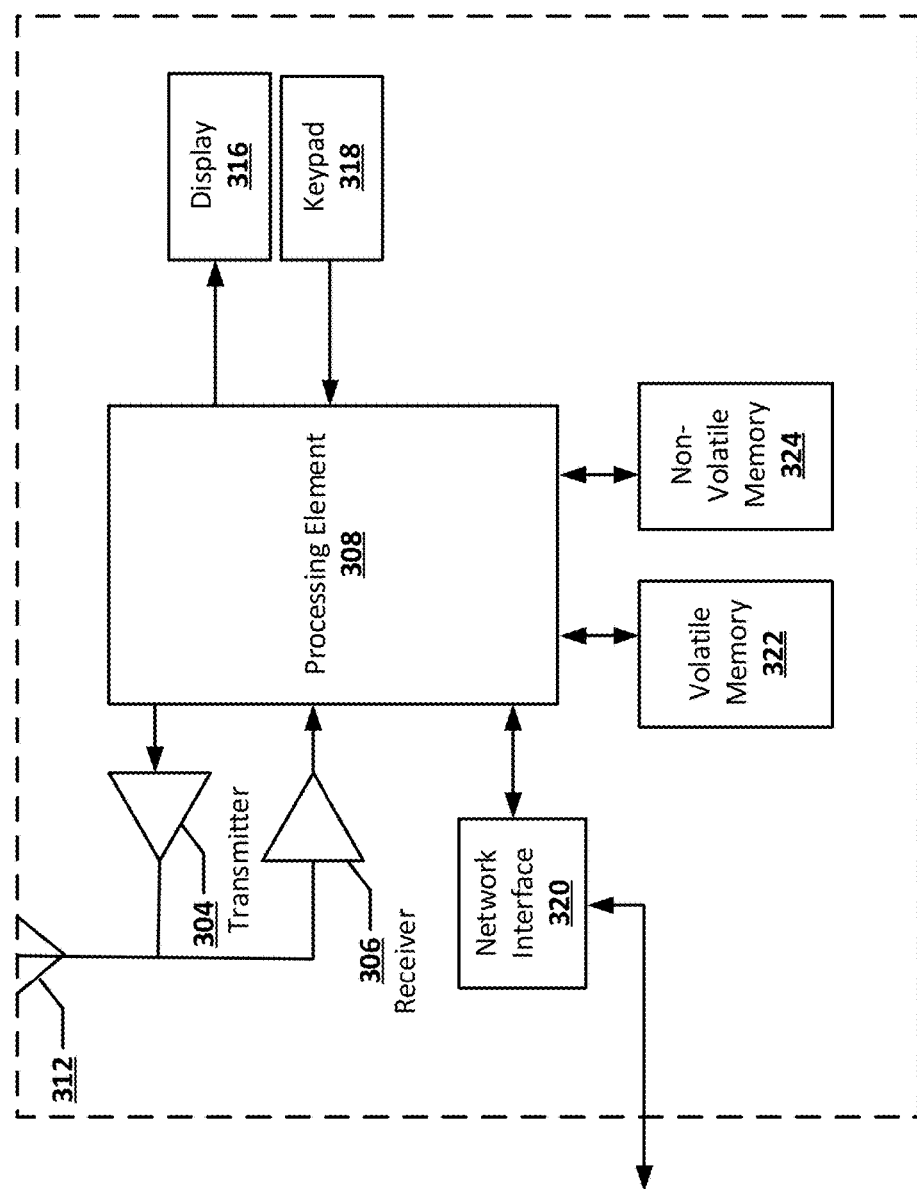
Figure 4:
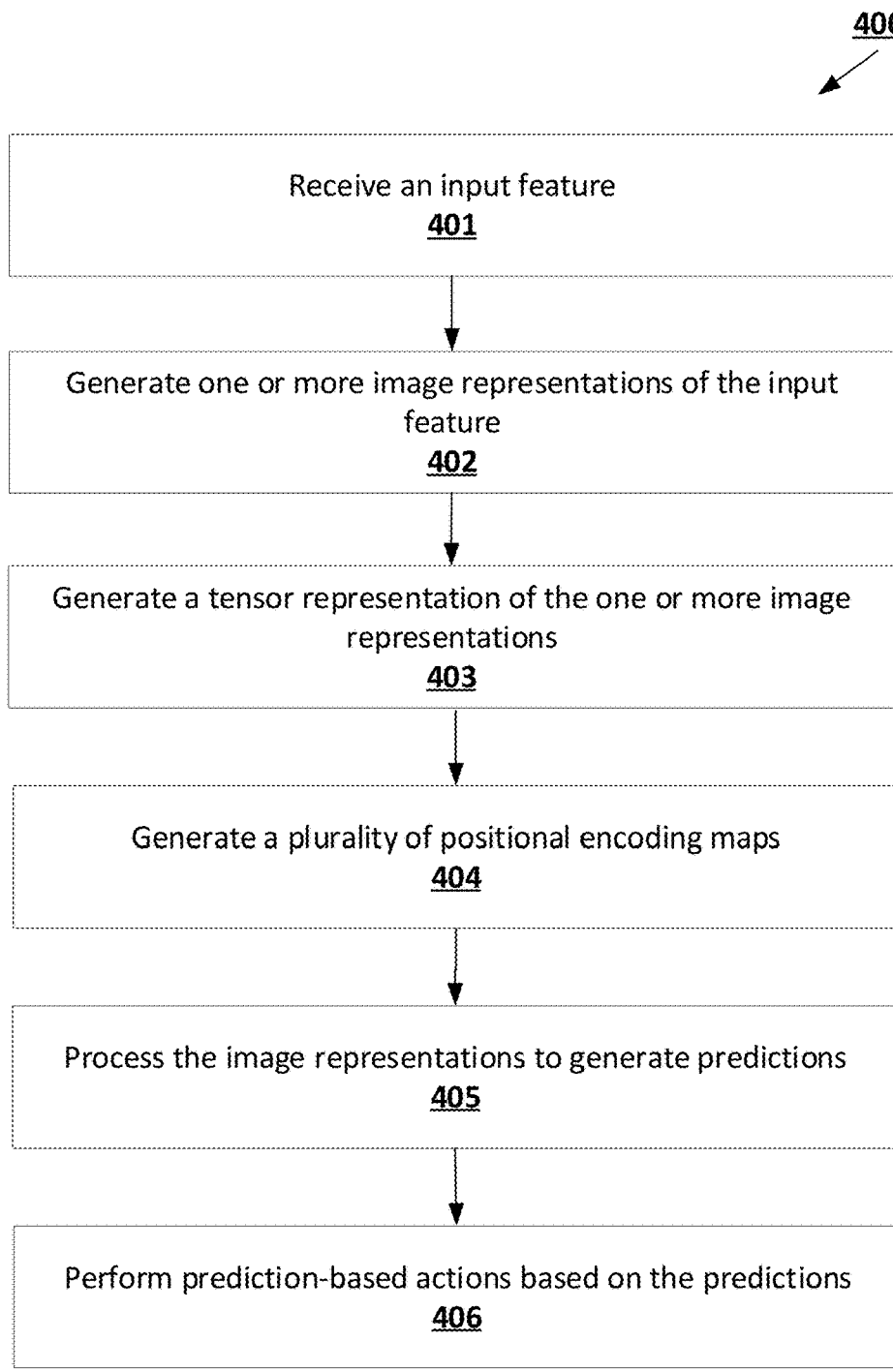
Figure 7:
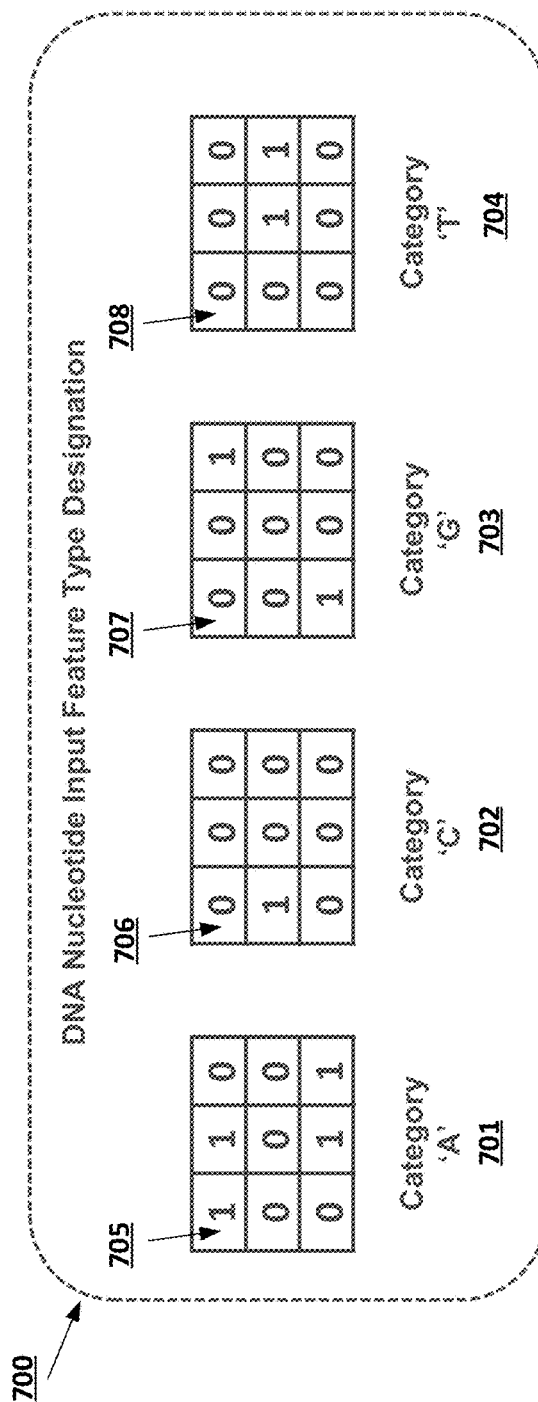
Figure 8:
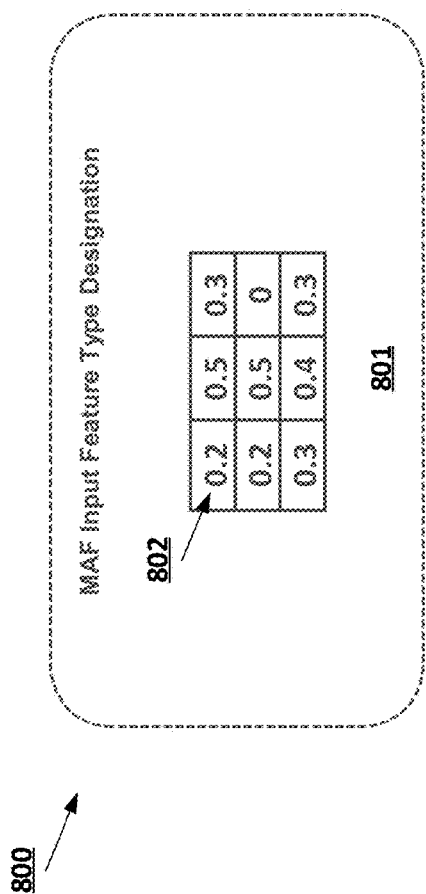
Figure 9:
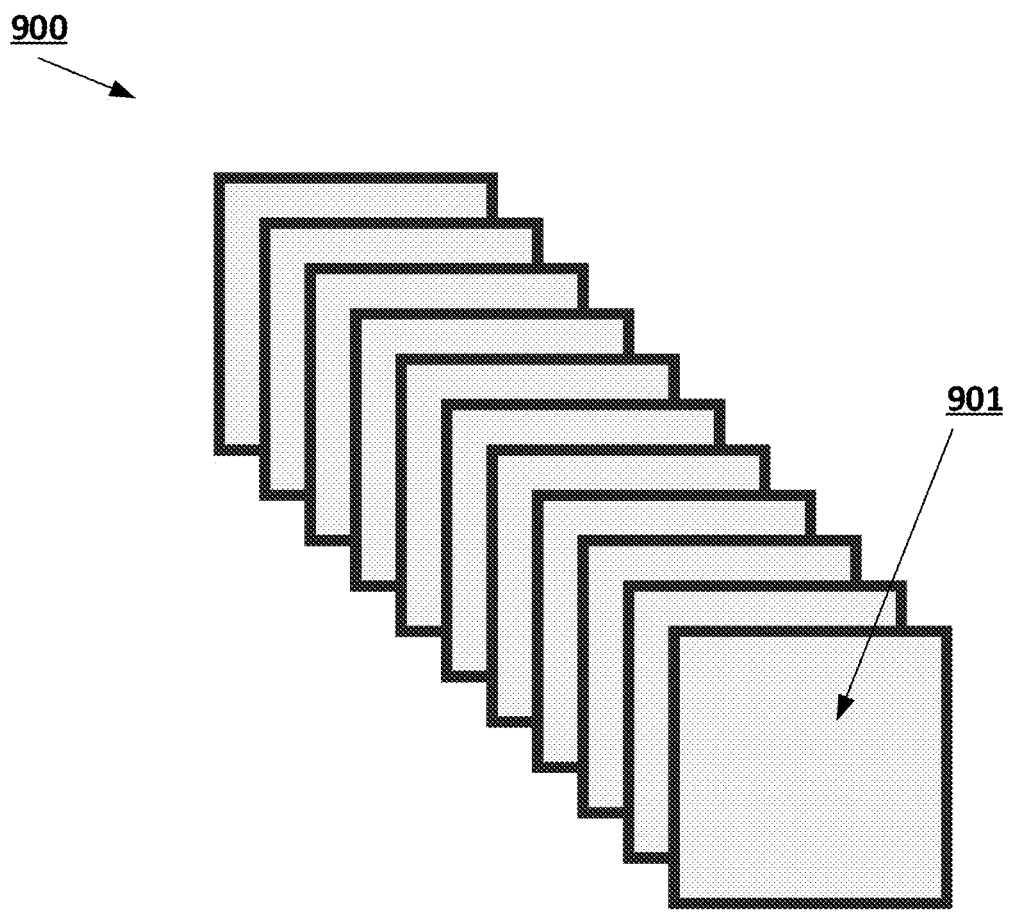
Figure 10:
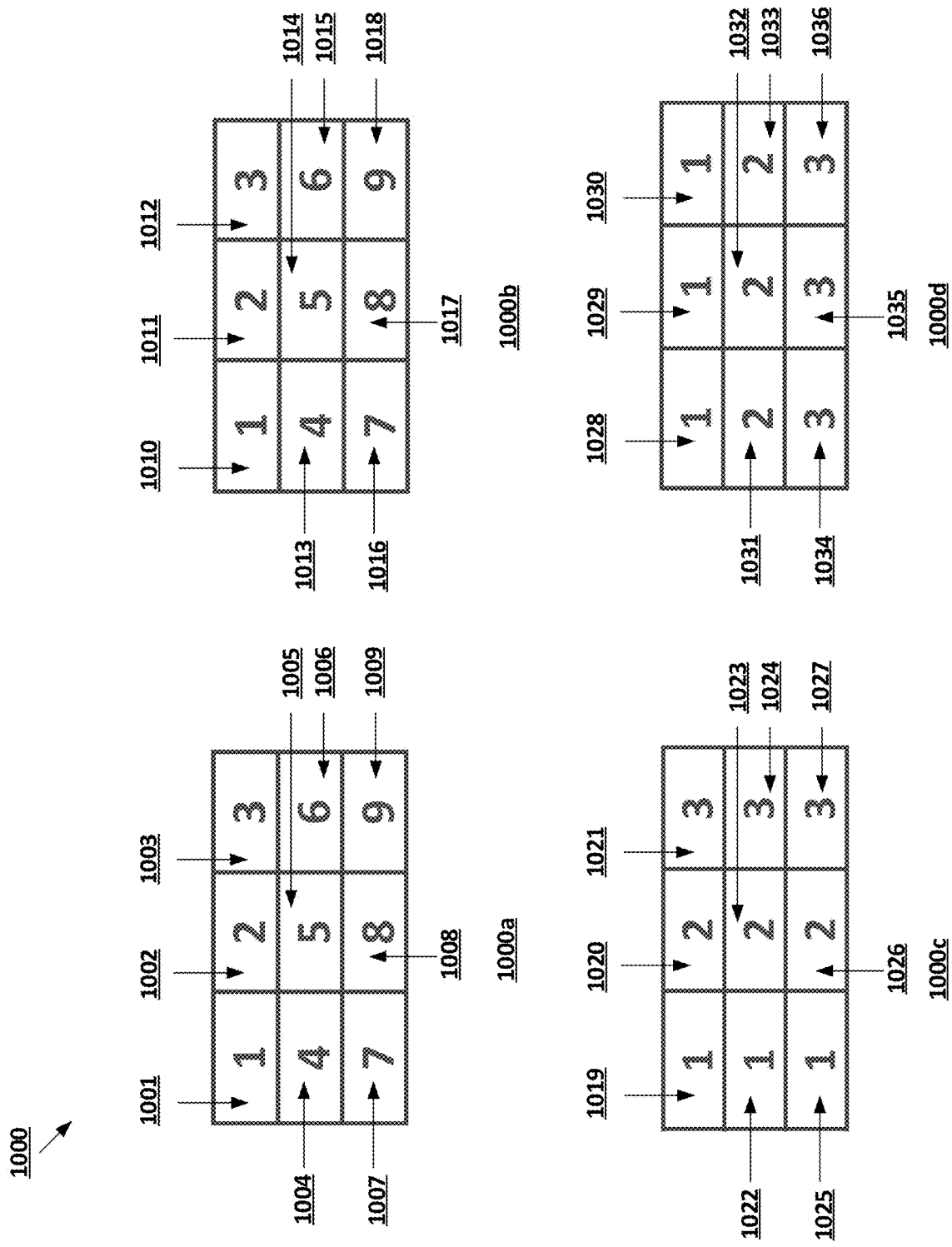
Figure 11:
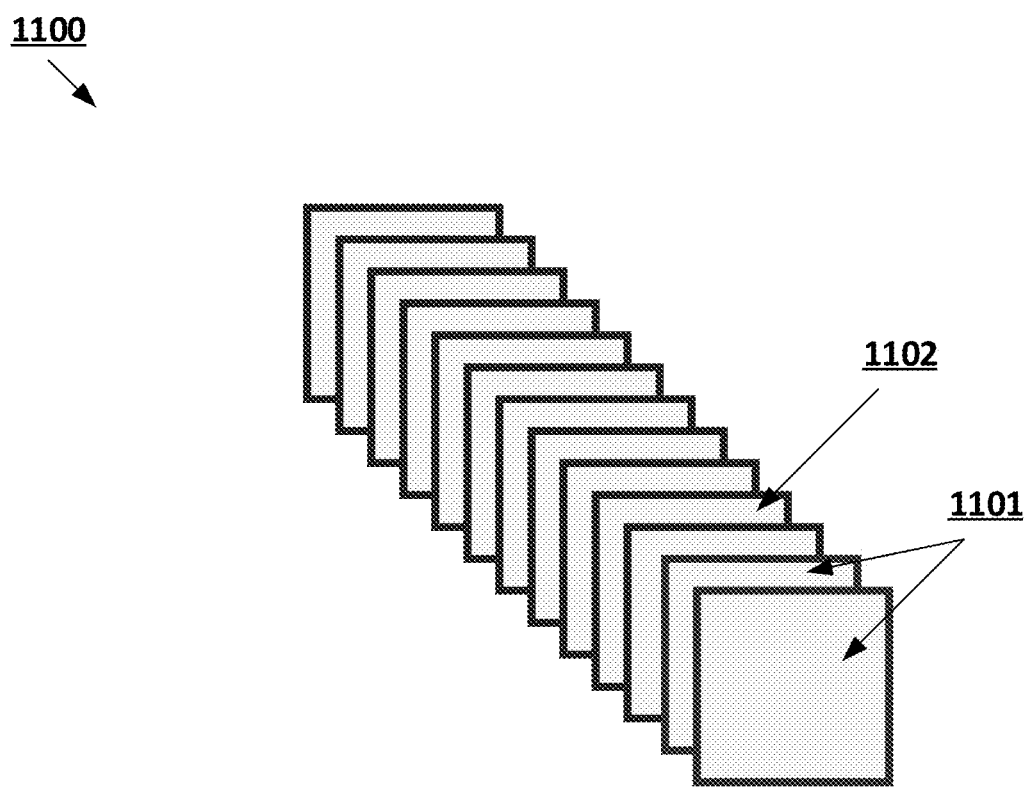
Figure 12:
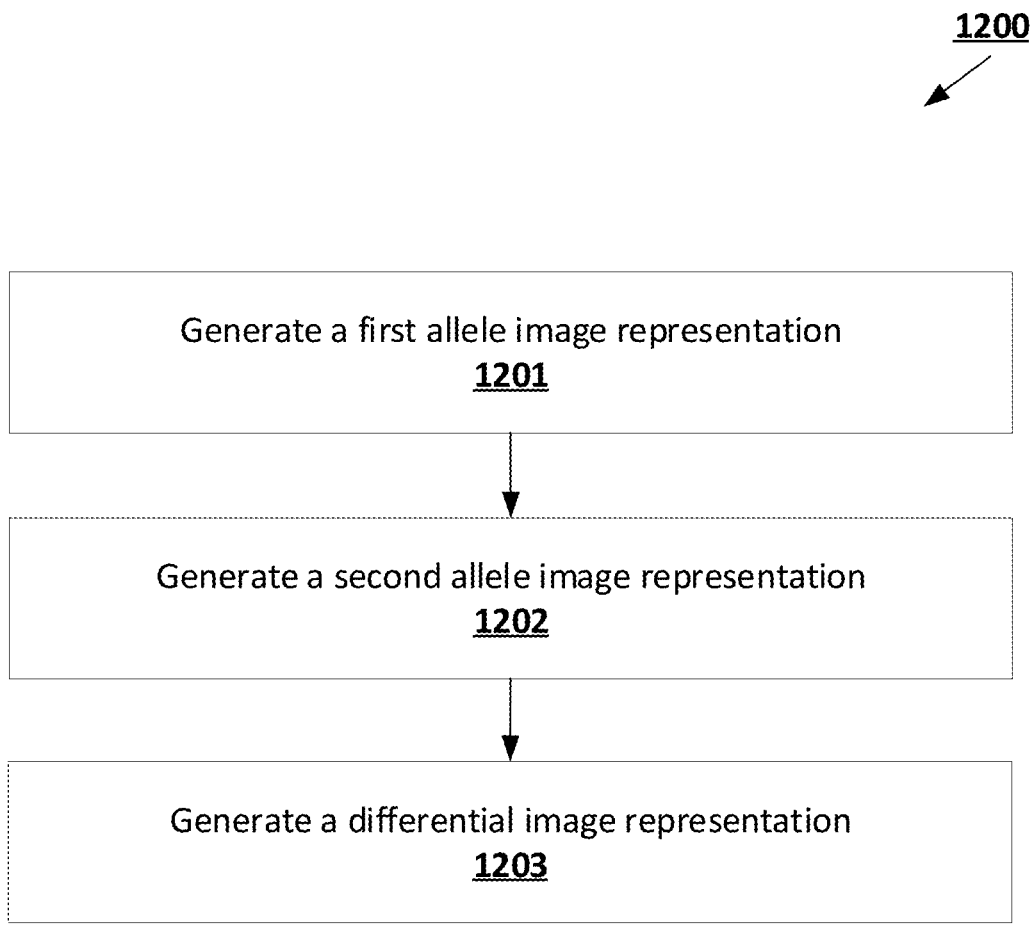
Figure 13:
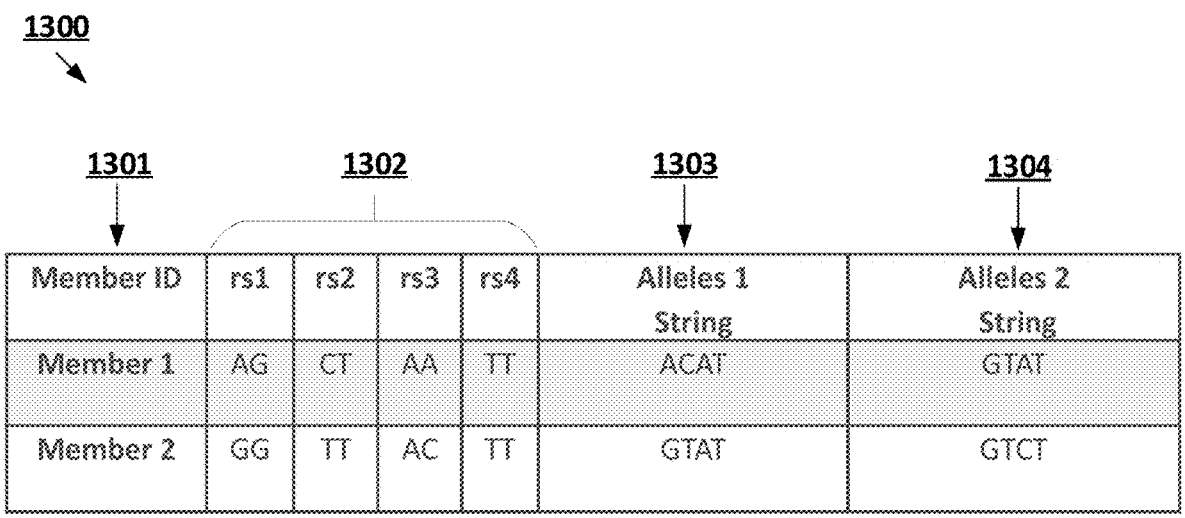
Figure 14B:
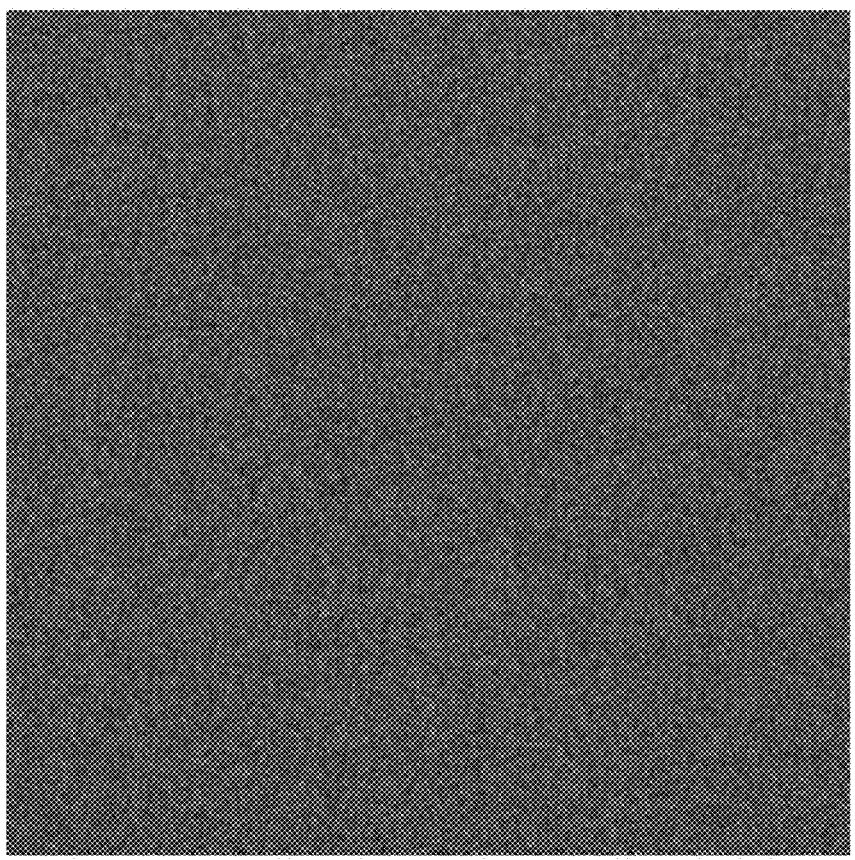
Figure 14A:
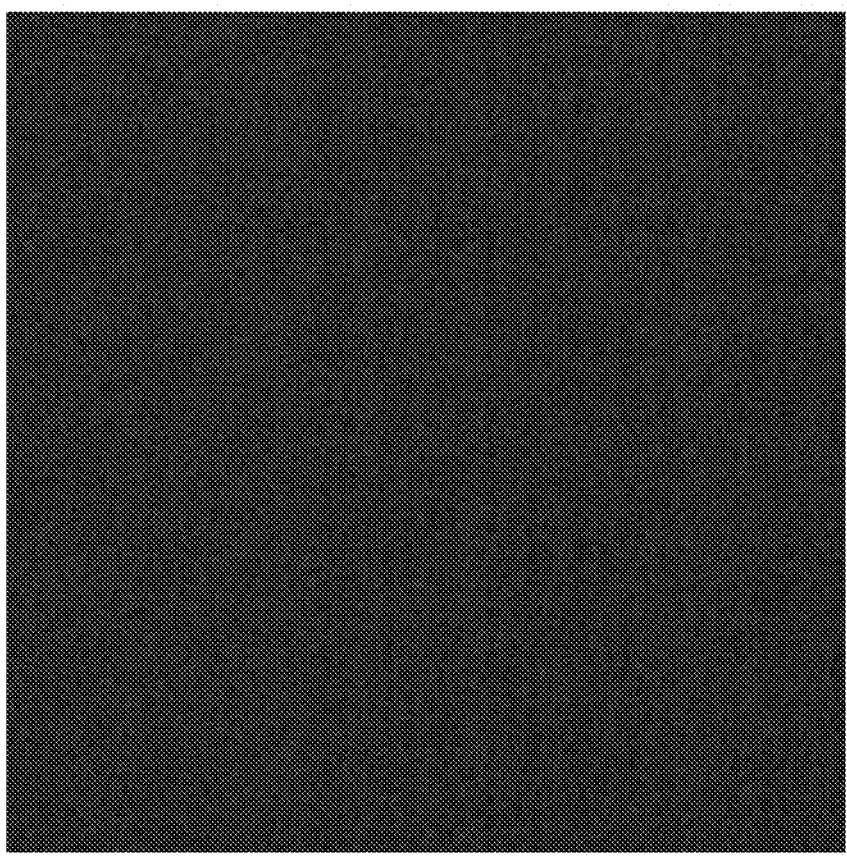
Figure 14D:
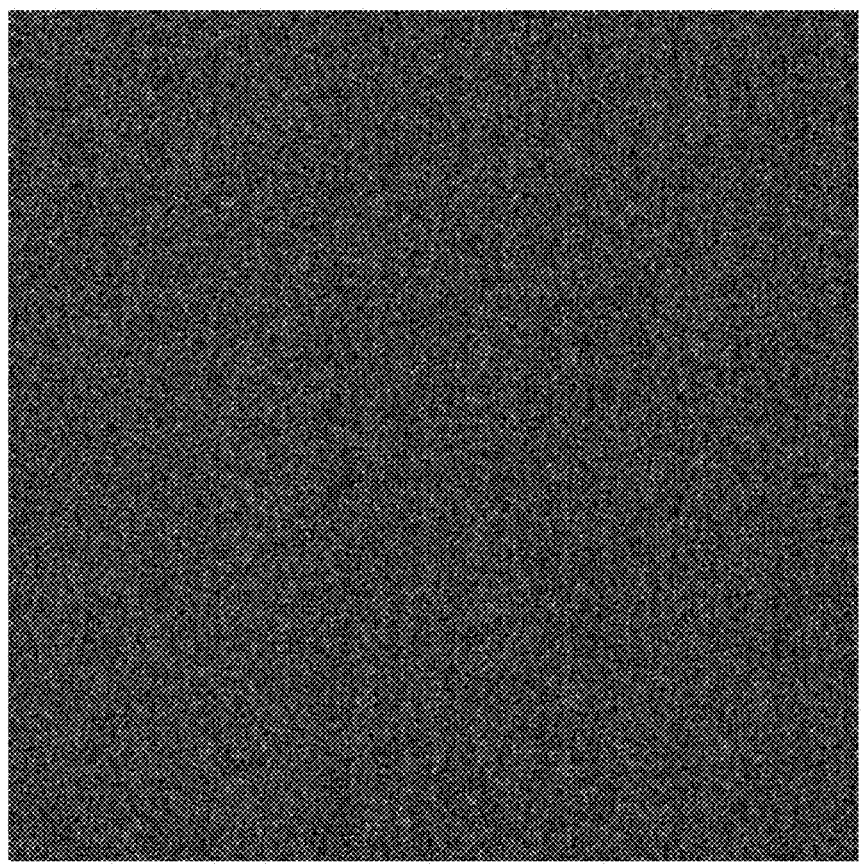
Figure 14C:
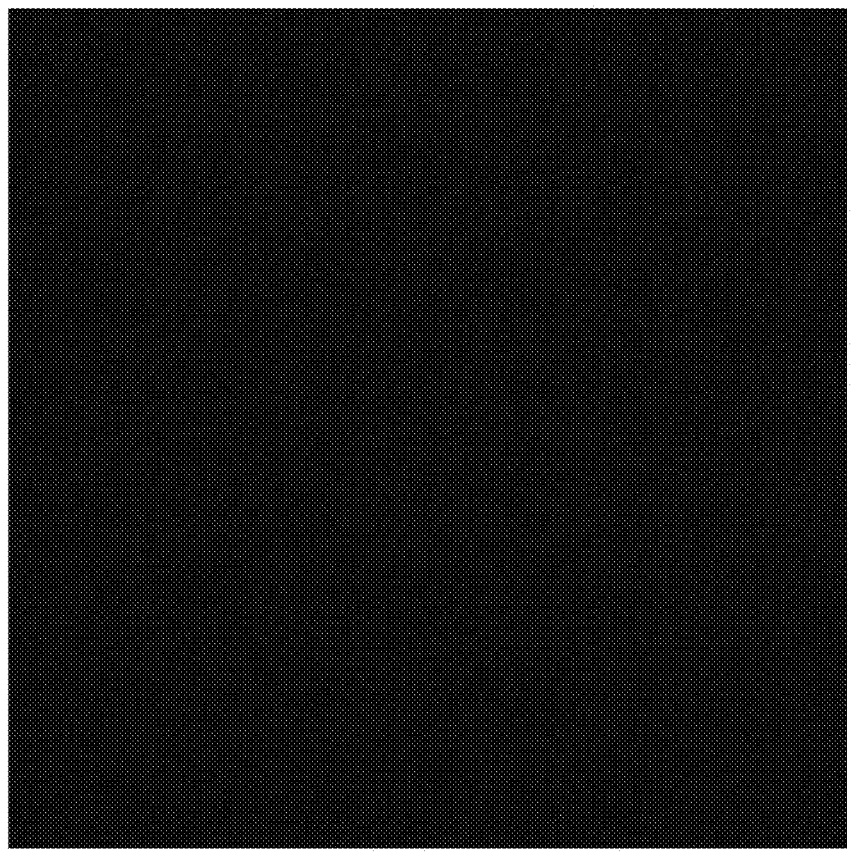
Figure 15:
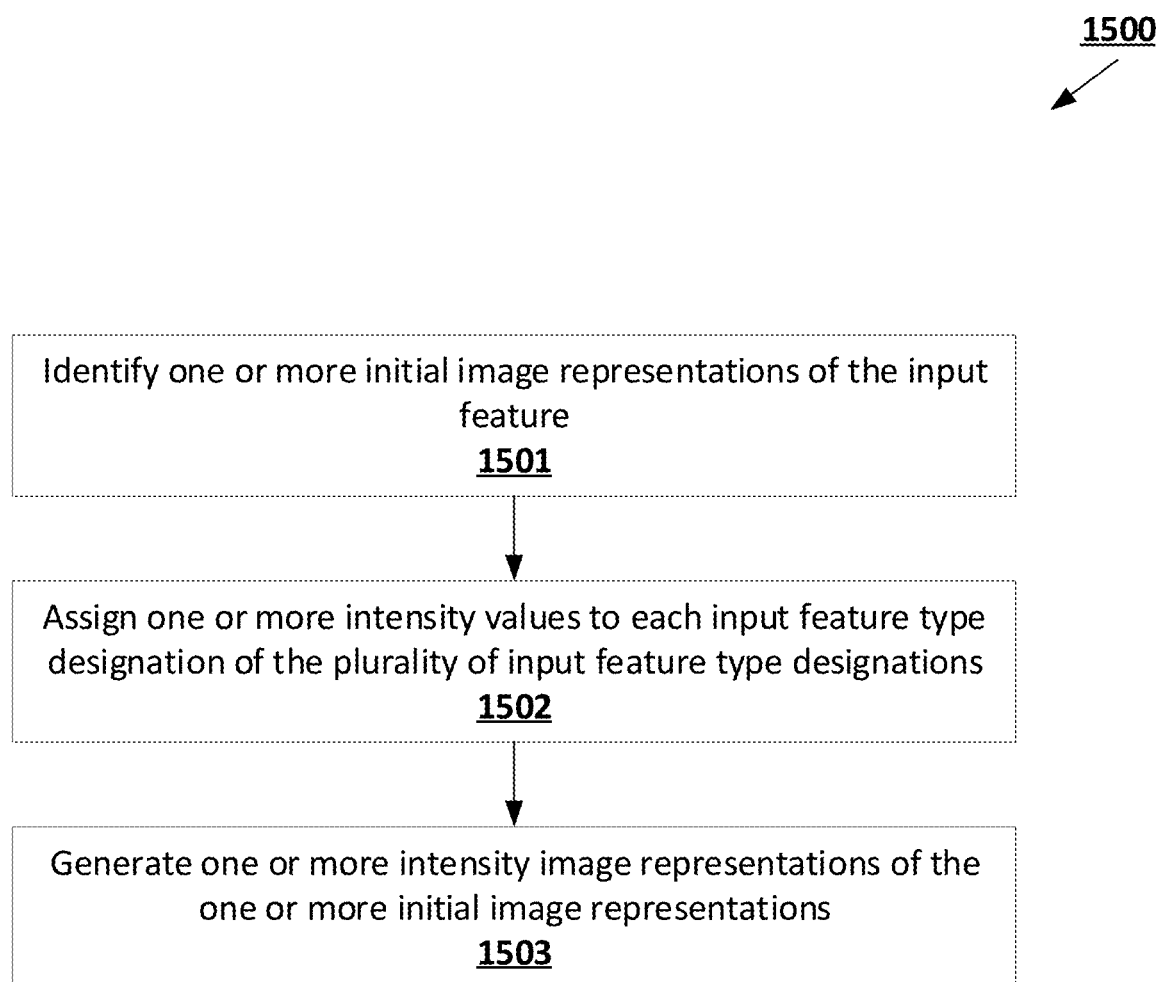
Figure 16:
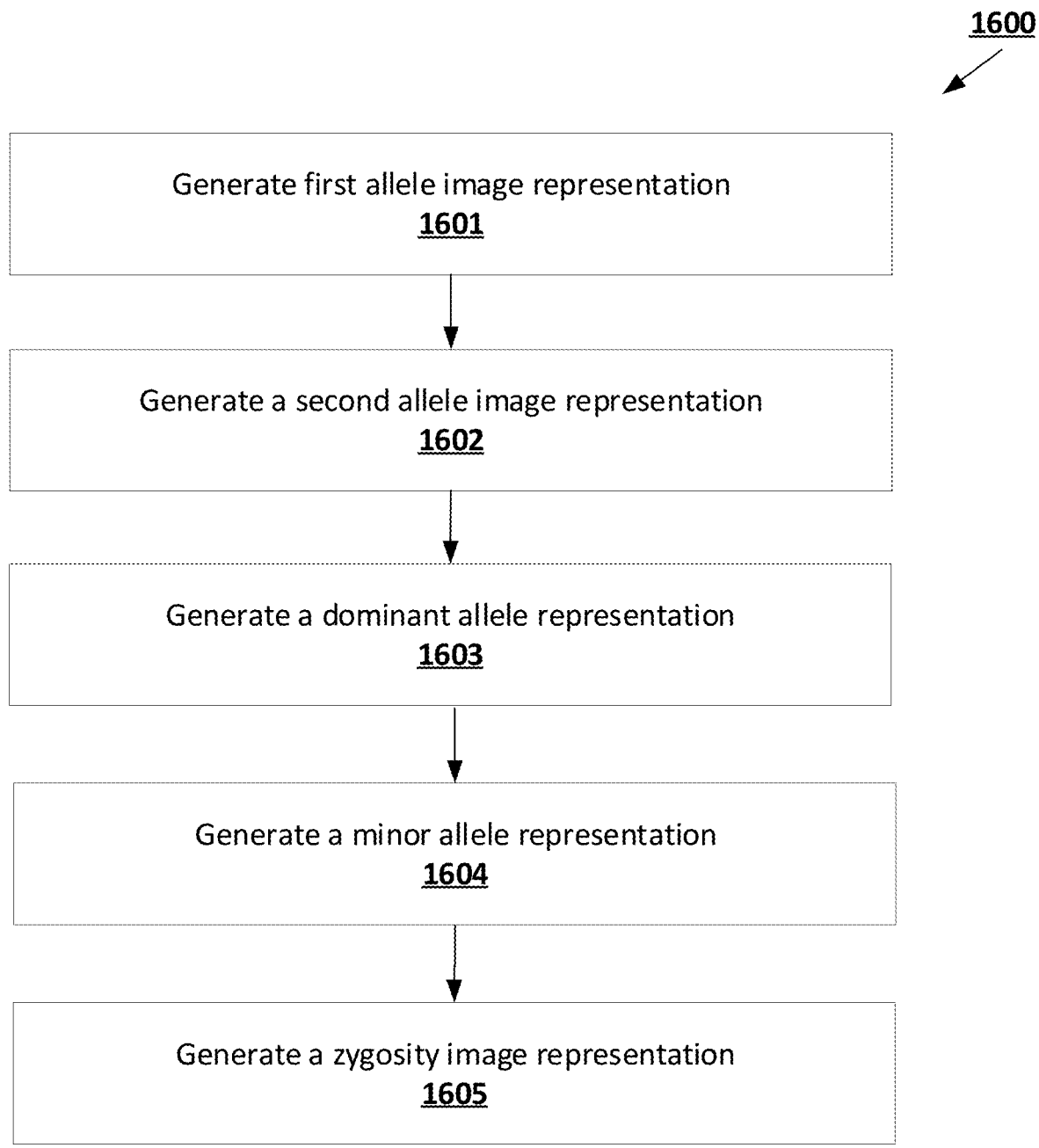
Figure 19:
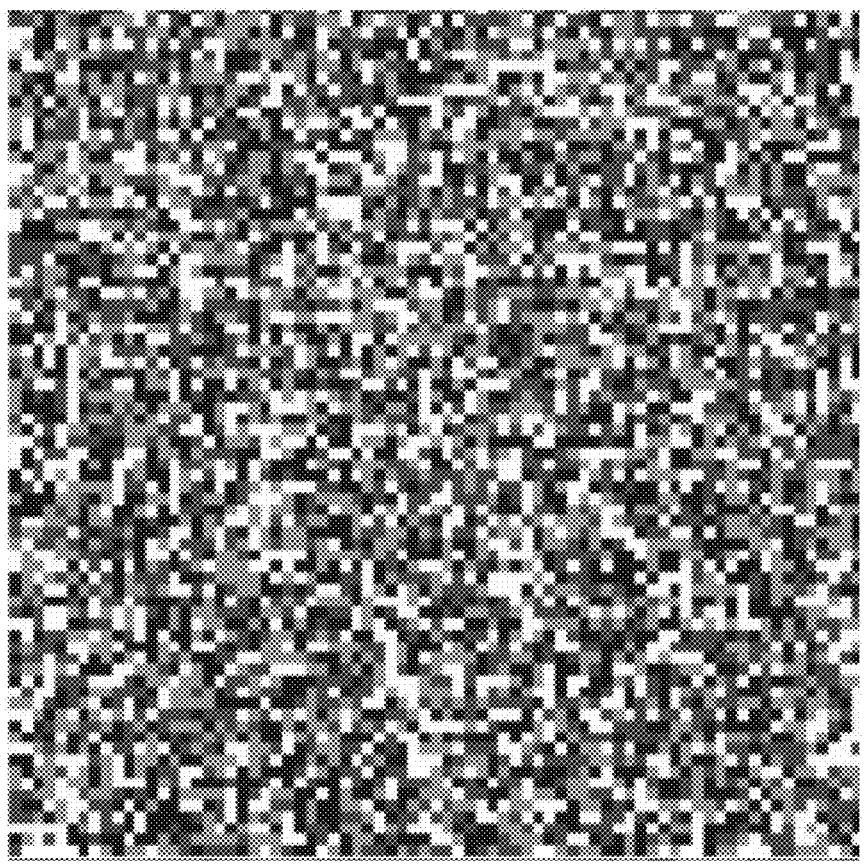
Figure 18:
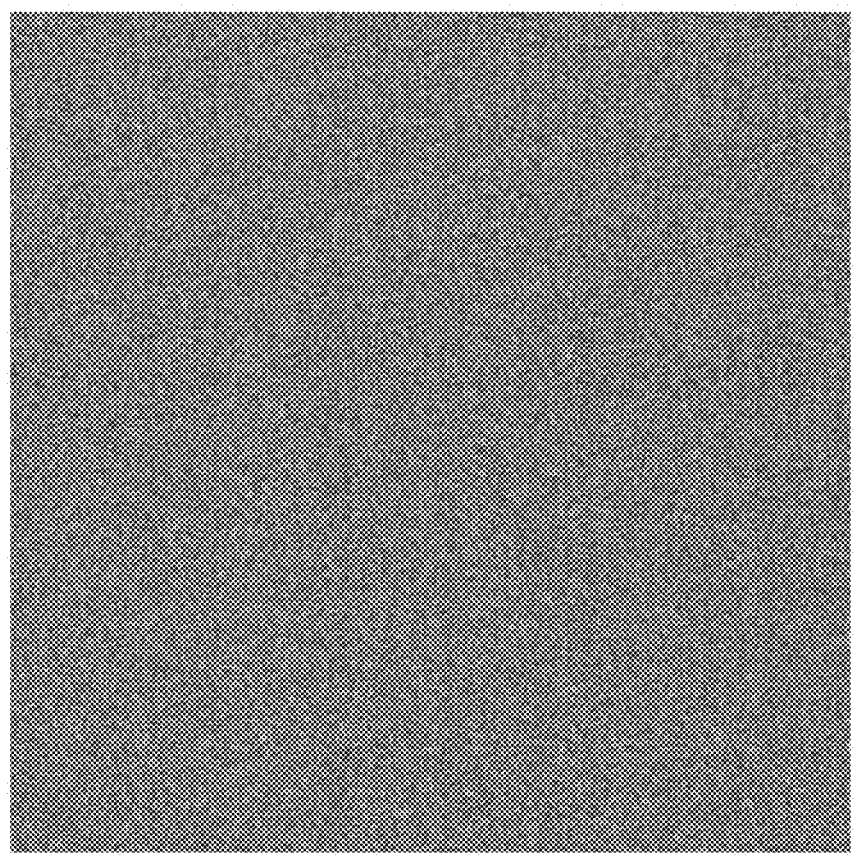
Figure 20:
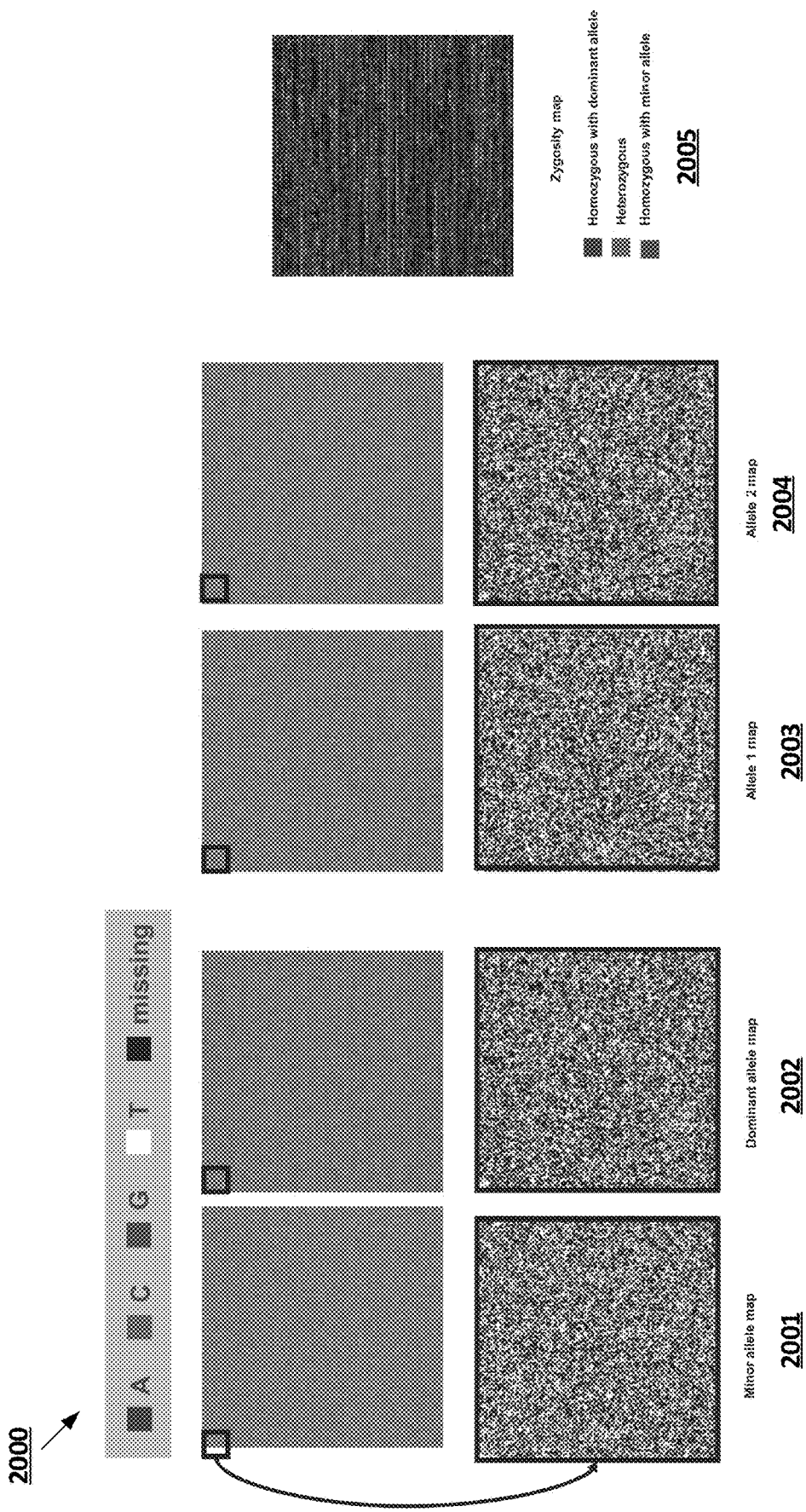
Figure 21:
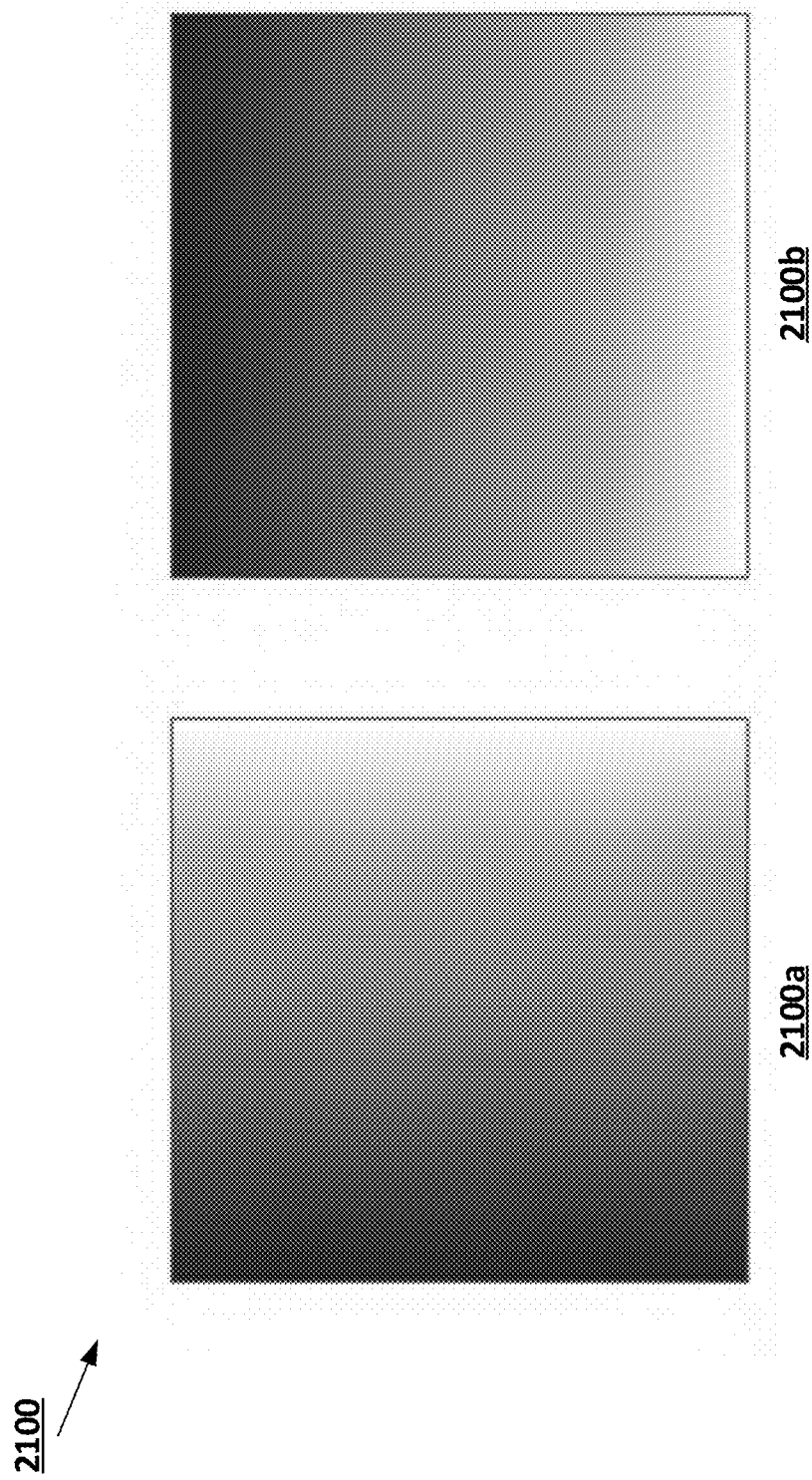
Figure 22:
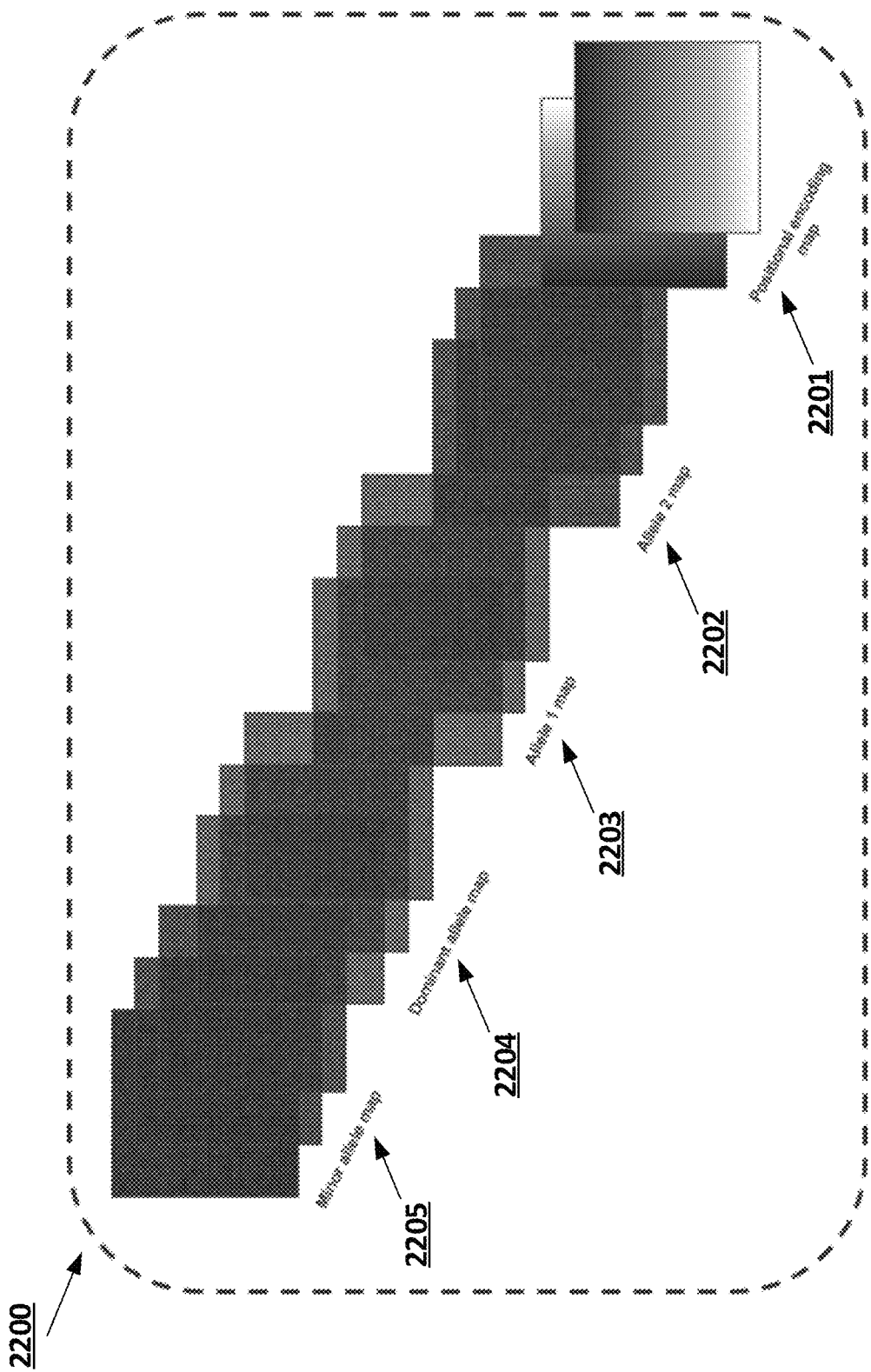
Figure 23:
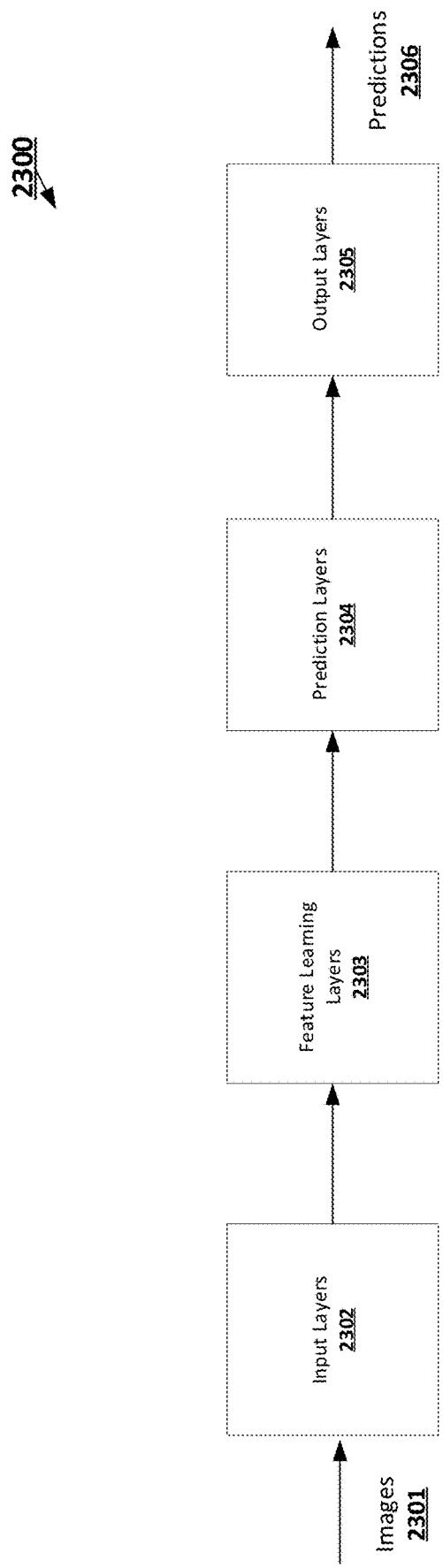
Figure 24:
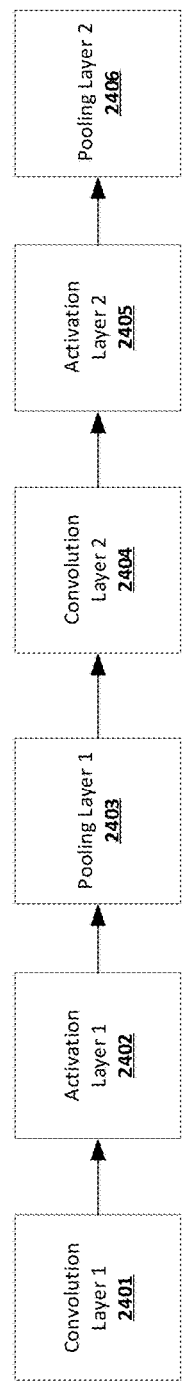
Figure 25:
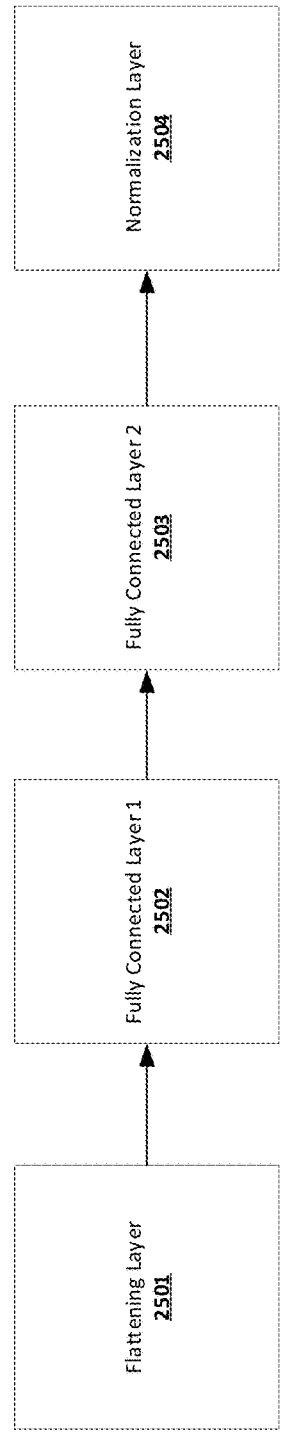
Figure 26:
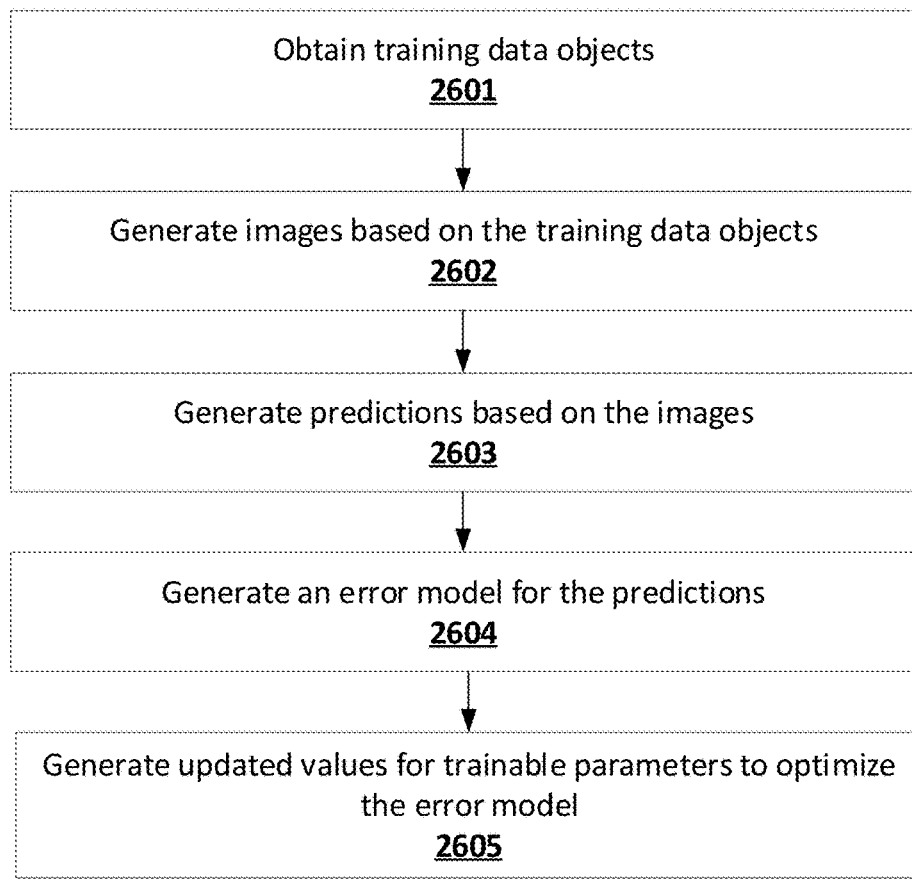

Having thus described the invention in general terms, reference will now be made to the accompanying drawings, which are not necessarily drawn to scale, and wherein:

FIG. 1 provides an exemplary overview of an architecture that can be used to practice embodiments of the present invention;

FIG. 2 provides an example predictive data analysis computing entity in accordance with some embodiments discussed herein;

FIG. 3 provides an example external computing entity in accordance with some embodiments discussed herein;

FIG. 4 is a flowchart diagram of an example process for performing image-based predictive data analysis in accordance with some embodiments discussed herein;

FIG. 5 provides an operational example of an example input feature in accordance with some embodiments discussed herein;

FIG. 6 provides an operational example of an example of image regions for an image representation in accordance with some embodiments discussed herein;

FIGS. 7-8 provide operational examples of an example image representations for a plurality of input feature type designations in accordance with some embodiments discussed herein;

FIG. 9 provides an operational example of a tensor representation in accordance with some embodiments discussed herein;

FIG. 10 provides an operational example of a plurality of positional encoding maps in accordance with some embodiments discussed herein;

FIG. 11 provides an operational example of a tensor representation with the plurality of positional encoding maps in accordance with some embodiments discussed herein;

FIG. 12 is a flowchart diagram of an example process for generating a differential image representation in accordance with some embodiments discussed herein;

FIG. 13 provides an operational example of an example input feature for a first allele and second allele in accordance with some embodiments discussed herein;

FIGS. 14A-D provide operational examples of example image representations for a input feature type designation in accordance with some embodiments discussed herein;

FIG. 15 is a flowchart diagram of an example process for generating an intensity image representation in accordance with some embodiments discussed herein;

FIG. 16 is a flowchart diagram of an example process for generating a zygosity image representation in accordance with some embodiments discussed herein;

FIG. 17 provides an operational example of an example input feature for a dominant allele and minor allele in accordance with some embodiments discussed herein;

FIGS. 18-19 provide operational examples of an allele image representation in accordance with some embodiments discussed herein;

FIG. 20 provides an operational example of a zygosity image representation in accordance with some embodiments discussed herein;

FIG. 21 provides an operational example of a plurality of positional encoding maps in accordance with some embodiments discussed herein;

FIG. 22 provides an operational example of a tensor representation in accordance with some embodiments discussed herein;

FIG. 23 is a block diagram of an example convolutional neural network architecture in accordance with some embodiments discussed herein;

FIG. 24 is a block diagram of an example convolutional layer set architecture for a convolutional neural network in accordance with some embodiments discussed herein;

FIG. 25 is a block diagram of an example prediction layer set architecture for a convolutional neural network in accordance with some embodiments discussed herein; and FIG. 26 is a flowchart diagram of an example process for training a machine learning model for performing image-based predictive data analysis in accordance with some embodiments discussed herein.

DETAILED DESCRIPTION

Various embodiments of the present invention are described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview and Technical Advantages

Discussed herein methods, apparatus, systems, computing devices, computing entities, and/or the like for predictive data analysis of an input feature by generating image representations based at least in part on the feature values comprising the input feature. As will be recognized, however, the disclosed concepts can be used to perform any type of data analysis, including non-predictive data analysis. Examples of predictive data analysis include supervised machine learning analysis (e.g., classification analysis and regression analysis) and unsupervised machine learning analysis (e.g., clustering analysis).

Many existing predictive data analysis solutions are incapable of efficiently and reliably performing predictive data analysis in prediction domains with complex input spaces. This is because many existing predictive data analysis solutions are developed for more common predictive data analysis tasks like image classification. For example, in the image classification domain, convolution neural networks (CNNs) have achieved tremendous success in efficiently and accurately performing predictive data analysis. Such solutions, however, are largely out of reach of developers in prediction domains with more complex input structures, such as prediction domains with high-dimensional categorical feature spaces. Thus, there is a technical need for predictive data analysis solutions that are capable of efficiently and reliably performing predictive data analysis in prediction domains with complex input spaces.

Genomic data is one such example of a domain associated with a high-dimensional feature space. To demonstrate the magnitude of the dimensional feature space associated with such genomic data, consider for example, that 3 billion nucleotides comprise the DNA of every human chromosome. A resulting FASTQ file size for a 30× coverage sequence for a single individual's DNA for each chromosome would be roughly around 100 gigabytes (GB), if uncompressed. Currently, genome-wide association studies (GWAS) have provided genomic data that has been utilized to investigate single-nucleotide polymorphism (SNP) point mutations, some of which may have casual associations with specific diseases. However, no current predictive data analysis system has been realized for conveniently representing SNP data or other genomic data such as copy-number variations (CNVs), insertions and deletions (indels), or other more complex genomic variants such as loss of heterozygosity (LOH). Furthermore, current predictive data analysis system do not allow for incorporation of DNA variants, transcriptome data, and epigenetic data, all of which have been shown to play a role in many diseases, such as cancer. As such, there is a need to represent genomic data in a form capable of being ingested by a predictive data analysis system such that the predictive data analysis system can process the genomic data in a meaningful way.

Various embodiments of the present invention address technical challenges related to efficiently and reliably performing predictive data analysis in complex prediction domains. For example, in some embodiments, proposed solutions disclose generating one or more image representations of an input feature comprising one or more feature values each corresponding to a genetic variant identifier and associated with an input feature type designation. Each image representation may comprise a plurality of image regions which correspond to a genetic variant identifier. The image representations may be further processed to generate a differential image representation, zygosity image representation, and intensity image representation. In some embodiments, a tensor representation of the one or more image representations is generated. Further in some embodiments, a plurality of positional encoding maps are generated and each genetic variant identifier is associated with a positional encoding map region set comprising each positional encoding map region associated with the genetic variant identifier across the plurality of positional encoding maps and are also included in the tensor representation. After generation, the tensor representation of the various image representations and/or positional encoding maps can be utilized by an image-based machine learning model (e.g., a machine learning model utilizing a CNN) to perform efficient and reliable predictive data analysis. The resulting machine learning solutions are more efficient to train and more reliable when trained. In doing so, various embodiments of the present invention address shortcomings of existing predictive data analysis solutions and enable solutions that are capable of efficiently and reliably performing predictive data analysis in prediction domains with complex input spaces.

II. Definitions of Certain Terms

The term "input feature" may refer to an electronically-received data construct that is configured to describe data pertaining to one or more individuals. In some embodiments, the input feature may comprise one or more feature values corresponding to a genetic variant identifier. Each feature value of the one or more feature values and each feature value may be associated with an input feature type designation of a plurality of input feature type designations. In some embodiments, the plurality of input feature type designations may include a DNA nucleotide, an RNA nucleotide, a minor allele frequency (MAF), a dominant allele frequency, and/or the like. In some embodiments, the one or more feature values correspond to a categorical feature type or numerical feature type. This may be dependent on which input feature type designation the feature value corresponds to. For example, a DNA nucleotide input feature type designation may be associated with feature values of a categorical feature input type, such as a feature value of "A", representative of the DNA nucleotide adenine. As another example, a MAF input feature type designation may be associated with features value of a numerical feature type, such as a feature value of 0.2. In some embodiments, a genetic variant identifier may be associated with one or more feature values and input feature type designations. For example, a particular genetic variant identifier may be associated with the feature value 'A', which may be a DNA nucleotide input feature type designation, and 0.2, which may be a MAF input feature type designation. Further, these particular feature values may be associated with one another. By way of continuing example, the feature value 'A' associated with a DNA nucleotide input feature type designation may have an associated minor allele frequency of 0.2 as indicated by the feature value 0.2 associated with a MAF input feature type designation corresponding to the same genetic variant identifier.

The term "genetic variant identifier" may refer to an electronically managed data construct indicative of a particular location on genetic material. In some embodiments, the genetic variant identifier is indicative of a particular single-nucleotide polymorphism (SNP) of a particular gene. In some embodiments, the genetic variant identifier is indicative of a particular position on a chromosome (i.e. a locus) and/or the identity of the particular chromosome. In some embodiments, the genetic variant identifier is merely representative of a particular location on genetic material. For example, a genetic variant identifier "rs1" may correspond to a particular gene locus, such as, for example, the first nucleotide locus for a particular gene and/or allele.

The term "image representation" may refer to an electronically managed data construct that is configured to describe, given a corresponding input feature having a plurality of input feature type designations, one or more image representations corresponding to each input feature type designations for the corresponding input feature each visually distinguishing the corresponding input feature. Furthermore, the image representation count of the one or more image representations may be based at least in part on the plurality of input feature type designations. For example, if an input feature is associated with a DNA nucleotide input feature designation type, which is a categorical feature type, an image representation for each category of the DNA nucleotide input feature designation type may be generated. As such, in this particular example, an image representation for a DNA nucleotide input feature designation type may include image representations corresponding to the DNA nucleotide categories adenine (A), thymine (T), cytosine (C), and guanine (G). As another example, if an input feature is associated with a MAF input feature designation type, which is a numerical feature type, only a single image representation may be generated.

The term "image representation region" may refer to an electronically managed data construct that is configured to describe a region of an image representation for a corresponding genetic variant identifier. The number of image representation regions may be determined based at least in part on the number of genetic variant identifiers such that each genetic variant identifier corresponds to an image representation region. In some embodiments, the visual representation of the image representation region may be indicative of at least whether a particular feature value corresponding to a particular genetic variant identifier is present or absent in the input feature.

The term "positional encoding map" may refer to an electronically managed data construct that is configured, within a plurality of position encoding maps comprising a plurality of positional encoding map region sets, to be indicative of data associated with a particular genetic variant identifier. A positional encoding map may be comprised of positional encoding map regions each corresponding to a genetic variant identifier. Each region of a positional encoding map may correspond to an identifier value. For example, the first positional encoding map region may comprise an identifier value of '1', the second positional encoding map region may comprise an identifier value of '2', etc. A positional encoding map set may comprise each positional encoding map region corresponding to the same genetic variant identifier across the plurality of positional encoding maps. For example, if the plurality of positional encoding maps comprise two positional encoding maps, and the positional encoding map regions corresponding to the first genetic variant identifier in both positional encoding maps comprise an identifier value of '1', the positional encoding map region set for the first genetic variant identifier may comprise the identifier values '1,1'.

The term "first allele image representation" may refer to an electronically managed data construct that is configured to describe a representation of a genetic sequence associated with an individual as indicated by feature values of an input feature associated with an individual. In some embodiments, the genetic sequence corresponds to one or more particular genes and/or alleles for a first chromosome and/or first set of chromosomes of the individual.

The term "second allele image representation" may refer to an electronically managed data construct that is configured to describe a representation of a genetic sequence associated with an individual as indicated by feature values of an input feature associated with an individual. In some embodiments, the genetic sequence corresponds to a particular gene and/or allele. In some embodiments, the genetic sequence corresponds to one or more particular genes and/or alleles for a second chromosome and/or second set of chromosomes of the individual. In some embodiments, the individual associated with the second allele image is the same individual associated with the first allele image representation. In some embodiments, the individual associated with the second allele image is a different individual than the individual associated with the first allele image representation.

The term "dominant allele image representation" may refer to an electronically managed data construct that is configured to describe a representation of a genetic sequence associated with a dominant genetic sequence for a particular genetic sequence as indicated by feature values of an input feature. In some embodiments, the genetic sequence corresponds to a particular gene and/or allele. In some embodiments, the dominant genetic sequence is the genetic sequence most common in a population.

The term "minor allele image representation" m may refer to an electronically managed data construct that is configured to describe a representation of a genetic sequence associated with a minor genetic sequence for a particular genetic sequence as indicated by feature values of an input feature. In some embodiments, the genetic sequence corresponds to a particular gene and/or allele. In some embodiments, the minor genetic sequence is the genetic sequence associated with a second most common genetic sequence in a population. In some embodiments, the minor genetic sequence is a genetic sequence associated other than the most common genetic sequence in a population.

The term "differential image representation" may refer to an electronically managed data construct that is configured to describe an image representation of a difference between a first image representation and a second image representation. In some embodiments, the differential image representation may be generated based at least in part on a comparison between a first allele image representation or second allele image representation and dominant allele image representation or minor allele image representation using one or more mathematical and/or logical operators. In some embodiments, the differential image representation may be generated based at least in part on a comparison between the first allele image representation and a second allele image representation corresponding to one or more individuals using one or more mathematical and/or logical operators. For example, if a first allele image representation indicates a feature value of 'A' in the image region corresponding to the first genetic variant identifier and a second allele image representation indicates a feature value of 'A' in the image region corresponding to the first genetic variant identifier, the image region of the differential image representation corresponding to the first genetic variant identifier may be indicative of a match between the first allele image representation and second allele image representation. As another example, if a first allele image representation indicates a feature value of 'A' in the image region corresponding to the second genetic variant identifier and a second allele image representation indicates a feature value of 'C' in the image region corresponding to the second genetic variant identifier, the image region of the differential image representation corresponding to the second genetic variant identifier may be indicative of a difference between the first allele image representation and second allele image representation. A match and/or difference in the image region for the differential image representation may be indicated in a variety of ways including using numerical values, colors, and/or the like. For example, a match between image regions in the first image representation and second image representation may be indicated by an image region value of '1' and a non-match between image regions in the first image representation and second image representation may be indicated by an image region value of '0'. As another example, a match between image regions in the first image representation and second image representation may be indicated by a white color in the corresponding image region while a non-match between image regions in the first image representation and second image representation may be indicated by a black color in the corresponding image region.

The term "zygosity image representation" may refer to an electronically managed data construct that is configured to describe a representation of a zygosity associated with an individual based at least in part on an associated first allele image representation and a second allele image representation for the individual, a dominant allele representation, and a minor allele representation for a genetic sequence (e.g. gene, allele, chromosome, etc.). In some embodiments, the zygosity image representation may be generated based at least in part on a comparison between the first allele image representation and a second allele image representation using one or more mathematical and/or logical operators, similar to the differential image representation. Further, the zygosity image representation may be generated based at least in part on a comparison between the between the first allele image representation, second allele image representation, dominant allele representation, and minor allele representation using one or more mathematical and/or logical operators. For example, if an individual is associated with a first allele image representation indicating a feature value of 'A' in the image region corresponding to the second genetic variant identifier and a second allele image representation indicates a feature value of 'C' in the image region corresponding to the second genetic variant identifier, the feature value for the second genetic variant identifier is determined to be heterozygous. As another example, if an individual is associated with a first allele image representation indicating a feature value of 'A' in the image region corresponding to the first genetic variant identifier and a second allele image representation indicates a feature value of 'A' in the image region corresponding to the first genetic variant identifier, the feature value for the first genetic variant is determine to be homozygous. Further, the homozygous feature value of 'A' may be compared to the feature values corresponding to the first genetic variant identifier in the dominant allele image representation and/or minor allele image representation. If the homozygous feature value matches the feature value in the dominant allele image representation, the feature value is determined to be homozygous with a dominant allele. If the homozygous feature value matches the feature value in the minor allele image representation, the feature value is determined to be homozygous with a minor allele. A heterozygous, homozygous with a dominant allele, homozygous with a minor allele, etc. may be indicated in a variety of ways including using values corresponding to each category, colors corresponding to each category, etc. For example, an image region determined to be heterozygous may be associated with a value of '0', an image region determined to be homozygous with a dominant allele may be associated with a value of '1', and an image region determined to be homozygous with a dominant allele may be associated with a value of '2'. As another example, an image region determined to be heterozygous may be associated with a green color, an image region determined to be homozygous with a dominant allele may be associated with a red color, and an image region determined to be homozygous with a dominant allele may be associated with a blue color.

The term "intensity image representation" may refer to an electronically managed data construct that is configured to describe feature values of an input feature type designation using one or more assigned intensity values for each input feature type designation. In some embodiments, input feature type designations associated with feature values corresponding to a categorical feature type may have an intensity value assigned for each category of the input feature type designation. For example, a DNA nucleotide input feature type designation may be associated with categories 'A', 'C', 'T', 'G', and missing (corresponding to adenine, cytosine, thymine, and guanine, respectively) may be assigned intensity values 1, 0.75, 0.5, 0.25, and 0. Additionally or alternatively, the categories 'A', 'C', 'T', 'G', and missing may be assigned intensity values corresponding to the colors red, green, blue, white, and black, respectively. In some embodiments, input feature type designations associated with feature values corresponding to a numeric feature type may have an intensity value based at least in part on the numeric value of the feature value. For example, a MAF input feature type designation may be associated with a numeric value between 0 and 1. As such, a feature value of '0.3' for an MAF input feature type designation may be associated with an intensity value of 0.3. In some embodiments, intensity value for a feature value corresponding to a numeric input feature type may be rounded to the nearest integer or decimal place of interest. For example, a feature value of 0.312 for an MAF input feature type designation may be associated with an intensity value of 0.3.

III. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware framework and/or operating system platform. A software component comprising assembly language instructions may require conversion into executable machine code by an assembler prior to execution by the hardware framework and/or platform. Another example programming language may be a higher-level programming language that may be portable across multiple frameworks. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatuses, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatuses, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Framework

FIG. 1 provides an exemplary overview of an architecture 100 that can be used to practice embodiments of the present invention. The architecture 100 includes a predictive data analysis system 101 and one or more external computing entities 102. For example, at least some of the one or more external computing entities 102 may provide prediction inputs to the predictive data analysis system 101 and receive predictive outputs from the predictive data analysis system 101 in response to providing the prediction inputs. As another example, at least some of the external computing entities 102 may provide prediction inputs to the predictive data analysis system 101 and request performance of particular prediction-based actions in accordance with the provided predictions. As a further example, at least some of the external computing entities 102 may provide training data objects to the predictive data analysis system 101 and request the training of a predictive model in accordance with the provided training data objects. In some of the noted embodiments, the predictive data analysis system 101 may be configured to transmit parameters and/or hyper-parameters of a trained machine learning model to the external computing entities 102.

In some embodiments, the predictive data analysis computing entity 106 and the external computing entities 102 may be configured to communicate over a communication network (not shown). The communication network may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis computing entity 106 may include a predictive data analysis computing entity 106 and a storage subsystem 108. The predictive data analysis computing entity 106 may be configured to train a prediction model based at least in part on the training data 122 stored in the storage subsystem 108, store trained prediction models as part of the model definition data 121 stored in the storage subsystem 108, utilize trained models to generate predictions based at least in part on prediction inputs provided by an external computing entity 102, and perform prediction-based actions based at least in part on the generated predictions. The storage subsystem may be configured to store the model definition data 121 for one or more predictive analysis models and the training data 122 uses to train one or more predictive analysis models. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

The predictive data analysis computing entity 106 includes a feature extraction engine 111, a predictive analysis engine 112, and a training engine 113. The feature extraction engine 111 may be configured to process prediction inputs to generate relevant processed features for predictive data analysis processing by the predictive analysis engine 112. For example, the feature extraction engine 111 may be configured to generate image representations of categorical feature data (e.g., as described with reference to FIGS. 4-22). The predictive analysis engine 112 may be configured to perform predictive data analysis based at least in part on the processed features generated by the feature extraction engine 111. For example, the predictive analysis engine 112 may be configured to perform image-based predictive data analysis (e.g., by using one or more CNNs, as for example described with reference to FIGS. 23-26) based at least in part on the image representations generated by the feature extraction engine. The training engine 113 may be configured to train at least one of the feature extraction engine 111 and the predictive analysis engine 112 in accordance with the training data 122 stored in the storage subsystem 108. Example operations of the training engine 113 are described with reference to FIG. 26.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, steps/operations, and/or processes described herein. Such functions, steps/operations, and/or processes may include, for example, transmitting, receiving, operating on, processing, displaying, storing, determining, creating/generating, monitoring, evaluating, comparing, and/or similar terms used herein interchangeably. In one embodiment, these functions, steps/operations, and/or processes can be performed on data, content, information, and/or similar terms used herein interchangeably.

As indicated, in one embodiment, the predictive data analysis computing entity 106 may also include a network interface 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include or be in communication with a processing element 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include or be in communication with non-volatile media (also referred to as non-volatile storage, memory, memory storage, memory circuitry and/or similar terms used herein interchangeably). In one embodiment, the non-volatile storage or memory may include at least one non-volatile memory 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the predictive data analysis computing entity 106 may further include or be in communication with volatile media (also referred to as volatile storage, memory, memory storage, memory circuitry and/or similar terms used herein interchangeably). In one embodiment, the volatile storage or memory may also include at least one volatile memory 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include a network interface 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include or be in communication with one or more input elements, such as a keyboard input, a mouse input, a touch screen/display input, motion input, movement input, audio input, pointing device input, joystick input, keypad input, and/or the like. The predictive data analysis computing entity 106 may also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, steps/operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (US SD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these frameworks and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a video capture device (e.g., camera), a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. Exemplary System Operations

To address the technical challenges associated with performing predictive data analysis in a computationally efficient and predictively reliable manner, various embodiments of the present invention describe a method, apparatus, systems, computing devices, computing entities, and/or the like for generating one or more image representation for an input feature comprising a plurality one or more feature values. Certain embodiments utilize systems, methods, and computer program products that perform predictive analysis of categorical data using image-based machine learning models (e.g., machine learning models that utilize CNNs).

Various embodiments of the present invention address technical challenges related to efficiently and reliably performing predictive data analysis in prediction domains. For example, in some embodiments, proposed solutions disclose generating one or more image representations of an input feature comprising one or more feature values, where each feature value corresponds to a genetic variant identifier and is associated with an input feature type designation. Each image representation may comprise a plurality of image regions, each corresponding to a genetic variant identifier. The image representations may be further processed to generate a differential image representation, zygosity image representation, and intensity image representation of input feature. A tensor representation of the one or more image representations may be generated. In some embodiments, a plurality of positional encoding maps are generated and each genetic variant identifier is associated with a positional encoding map region set comprising each positional encoding map region associated with the genetic variant identifier across the plurality of positional encoding maps and are also included in the tensor representation. After generation, the tensor representation of the various image representations and/or positional encoding maps can be utilized by an image-based machine learning model (e.g., a machine learning model utilizing a CNN) to perform efficient and reliable predictive data analysis. The resulting machine learning solutions are more efficient to train and more reliable when trained.

Image-Based Predictive Inference

FIG. 4 is a flowchart diagram of an example process 400 for performing image-based predictive data analysis. Via the various steps/operations of process 400, the predictive data analysis computing entity 106 may process an input feature (e.g., structured text input features) to generate an image-based prediction. The predictive data analysis computing entity 106 may then utilize image-based machine learning solutions (e.g., solutions utilizing CNNs) to infer predictive insights from the input feature, such as structured text input features.

At step/operation 401, the feature extraction engine 111 of the predictive data analysis computing entity 106 receives an input feature. Examples of an input feature include structured text input features, including feature data associated with a predictive entity. For example, the input feature may describe data pertaining to one or more individuals. In some embodiments, the input feature may comprise one or more feature values corresponding to a genetic variant identifier. Each feature value of the one or more feature values and each feature value may be associated with an input feature type designation of a plurality of input feature type designations. In some embodiments, the plurality of input feature type designations may include a DNA nucleotide, an RNA nucleotide, a minor allele frequency (MAF), a dominant allele frequency, and/or the like.

In some embodiments, the one or more feature values correspond to a categorical feature type or numerical feature type. This may be dependent on which input feature type designation the feature value corresponds to. For example, a DNA nucleotide input feature type designation may be associated with feature values of a categorical feature input type, such as a feature value of "A", representative of the DNA nucleotide adenine. As another example, a MAF input feature type designation may be associated with features value of a numerical feature type, such as a feature value of 0.2. In some embodiments, a genetic variant identifier may be associated with one or more feature values and input feature type designations. For example, a particular genetic variant identifier may be associated with the feature value 'A', which may be a DNA nucleotide input feature type designation, and 0.2, which may be a MAF input feature type designation. Further, these particular feature values may be associated with one another. By way of continuing example, the feature value 'A' associated with a DNA nucleotide input feature type designation may have an associated minor allele frequency of 0.2 as indicated by the feature value 0.2 associated with a MAF input feature type designation corresponding to the same genetic variant identifier.

An operational example of an input feature 500 is depicted in FIG. 5. By way of example, an input feature may comprise feature values "A", "A", "G", "C", "T", "T", "G", "A", and "A" corresponding to the input feature type designation DNA nucleotide 502 and feature values "0.2", "0.5", "0.3", "0.2", "0.5", "0", "0.3", "0.4", "0.3" corresponding to the input feature type designation MAF 503. Additionally, each feature value of the input feature may correspond to a genetic variant identifier 501.

In some embodiments, the feature extraction engine 111 may identify one or more feature values from an input feature structured as a text sequence. The feature extraction engine 111 may identify the one or more feature values in a variety of ways, such as by using a delimiter. For example, the boundary between separate feature values of the input feature may be indicated by a predefined character such as a comma, semicolon, quotes, braces, pipes, slashes, etc. In the above example, a boundary between feature values may be indicated by a comma such that structured text sequence "A,A,G,C,T,T,G,A,A" corresponds to feature values "A", "A", "G", "C", "T", "T", "G", "A", and "A". Additionally or alternatively, in some embodiments, the feature extraction engine 111 may identify one or more feature values based at least in part on the input feature type designation of a structured text sequence. For example, an input feature comprising the structured text sequence "AAGCTTGAA" may correspond to a DNA nucleotide input feature type designation. A feature extraction engine 111 may be configured to automatically identify each character comprising the structured text sequence associated with a DNA nucleotide input feature type designation such that the feature extraction engine 111 may automatically identify the feature values "A", "A", "G", "C", "T", "T", "G", "A", and "A" without the use of delimiters.

At step/operation 402, the feature extraction engine 111 generates one or more image representations based at least in part on the input feature obtained/received in step/operation 401. In some embodiments, to generate the one or more image representations based at least in part on the input feature, the feature extraction engine 111 retrieves configuration data for a particular image-based processing routine from the model definition data 121 stored in the storage subsystem 108. Examples of the particular-image-based processing routines are discussed below with reference to FIGS. 5-22. However, one of ordinary skill in the art will recognize that the feature extraction engine 111 may generate the one or more images by applying any suitable technique for transforming the input feature into the one or more images. In some embodiments, the feature extraction engine 111 selects a suitable image-based processing routine for the input feature given the one or more properties of the input feature (e.g., inclusion of input feature type designations for the input feature, an indication of feature values pertaining to one or more individuals, and/or the like). In some embodiments, the feature extraction engine 111 may select a suitable image-based processing routine for the input feature based at least in part on a user specified preference. In some embodiments, the user specified preference may be indicated in the input feature.

An operational example of generating one or more image representations 600 is depicted in FIG. 6. As previously described, each feature value of the input feature may correspond to a genetic variant identifier. As such, the feature extraction engine 111 may determine an image representation configuration 600 comprising one or more image regions 601-609. Each image region 601-609 may correspond to a genetic variant identifier as described by the input feature received in step/operation 401. For example, if the input feature comprises feature values corresponding to nine genetic variant identifiers, the feature extraction engine 111 may determine an image representation configuration 600 comprising nine image regions. The image representation configuration 600 may then be used when generating the one or more image representations. Each of the one or more image regions may comprise one or more pixels and be associated with a length dimension and width dimension. In some embodiments, each of the one or more image regions may comprise the same number of pixels. In some embodiments, each of the one or more image regions may comprise the same length dimension and width dimension.

In some embodiments, the image representation configuration 600 is associated with a length dimension and width dimensions based at least in part on the length dimension and width dimension of each of the one or more image regions. In some embodiments, the arrangement of the one or more image regions comprising the image representation configuration 600 may be determined by the feature extraction engine 111. In some embodiments, the feature extraction engine 111 may determine the arrangement of the one or more image regions comprising the image representation configuration 600 based at least in part on the length dimension and width dimension of the one or more image regions. In some embodiments, the feature extraction engine 111 may determine the arrangement of the one or more image regions comprising the image representation configuration 600 such that values of the length dimension and width dimension of the image representation configuration 600 are as close as possible. For example, the feature extraction engine 111 may determine a length dimension value of 3 and width dimension value of 3 for an image representation configuration 600 comprising nine image regions each comprising a length dimension of 1 pixel and a width dimension of 1 pixel. As such, the image representation configuration may be square or rectangular in shape.

In some embodiments, the feature extraction engine 111 may determine to order the image regions each corresponding to a genetic variant identifier in order of the one or more genetic variant identifier such that each image region corresponding to a genetic variant identifier is adjacent to the image region corresponding to the next sequential genetic variant identifier. For example, as shown in FIG. 6, an image region 601 corresponding to a genetic identifier rs1 is adjacent to an image region 602 corresponding to a genetic identifier rs2. As another example, an image region 601 corresponding to a genetic identifier rs1 may also be adjacent to an image region 604 corresponding to a genetic identifier rs2 (not shown in FIG. 6).

An operational example of generating one or more image representations 700 for a categorical feature type is depicted in FIG. 7. In this particular example, a DNA nucleotide input feature type designation is shown, wherein the DNA nucleotide input feature type designation is a categorical input feature type. In particular, the DNA nucleotide input feature type designation is associated with 4 categories, 'A', 'C', 'G', and 'T'. Each category of the DNA nucleotide input feature type designation has a corresponding image representation 701-704. The image representation for each category is based at least in part on the image representation configuration depicted in FIG. 6 and the feature values of the input feature. For example, if the feature value for the first genetic identifier rs1 is 'A', the value of the image region corresponding to the first genetic identifier rs1 for the image representation for the category 'A' may be affirmative of the value 'A'. This may be communicated in a variety of ways, such as by a binary system where 1 indicates the presence of the corresponding category and where 0 indicates the absence of the corresponding category for each genetic variant identifier. In this instance, since the feature value for the first genetic identifier rs1 is 'A', the image region 705 corresponding to the first genetic identifier for the category 'A' is assigned a value of 1 and the image regions 706-708 corresponding to the first genetic identifier for the categories 'C', 'G', and 'T' is assigned a value of 0.

An operational example of generating one or more image representations 800 for a numerical feature type is depicted in FIG. 8. In this particular example, a MAF input feature type designation is shown, wherein the MAF input feature type designation is a numerical input feature type. In contrast to categorical input feature types, numerical input feature types may only be associated with one image representation. The image representation 801 is based at least in part on the image representation configuration depicted in FIG. 6 and the feature values of the input feature. For example, if the feature value for the first genetic identifier rs1 is '0.2', the value of the image region corresponding to the first genetic identifier rs1 for the image representation may be '0.2'. In this instance, since the feature value for the first genetic identifier rs1 is '0.2', the image region 802 is assigned a value of '0.2'.

In some embodiments, step/operation 402 may be performed in accordance with the various steps/operations of the process 1200 that depicted in FIG. 12, which is a flowchart diagram of an example process for generating a differential image representation.

The process 1200 depicted in FIG. 12 begins at step/operation 1201, when the feature extraction engine 111 generates a first allele image representation. In some embodiments, an input feature may describe a representation of a genetic sequence associated with an individual as indicated by feature values of an input feature associated with an individual. In some embodiments, the genetic sequence corresponds to one or more particular genes and/or alleles for a first chromosome and/or first set of chromosomes of the individual. The first allele image representation may be generated substantially similarly to the process described in step/operation 402.

At step/operation 1202, the feature extraction engine 111 generates a second allele image representation. In some embodiments, an input feature may describe a representation of a genetic sequence associated with an individual as indicated by feature values of an input feature associated with an individual. In some embodiments, the genetic sequence corresponds to one or more particular genes and/or alleles for a second chromosome and/or second set of chromosomes of the individual. In some embodiments, the individual associated with the second allele image is the same individual associated with the first allele image representation. In some embodiments, the individual associated with the second allele image is a different individual than the individual associated with the first allele image representation. The second allele image representation may be generated substantially similarly to the process described in step/operation 402.

At step/operation 1203, the feature extraction engine 111 generates a differential image representation. In some embodiments, the differential image representation may be generated based at least in part on a comparison between a first allele image representation or second allele image representation and dominant allele image representation or minor allele image representation using one or more mathematical and/or logical operators. In some embodiments, the differential image representation may be generated based at least in part on a comparison between the first allele image representation and a second allele image representation corresponding to one or more individuals using one or more mathematical and/or logical operators. For example, if a first allele image representation indicates a feature value of 'A' in the image region corresponding to the first genetic variant identifier and a second allele image representation indicates a feature value of 'A' in the image region corresponding to the first genetic variant identifier, the image region of the differential image representation corresponding to the first genetic variant identifier may be indicative of a match between the first allele image representation and second allele image representation.

As another example, if a first allele image representation indicates a feature value of 'A' in the image region corresponding to the second genetic variant identifier and a second allele image representation indicates a feature value of 'C' in the image region corresponding to the second genetic variant identifier, the image region of the differential image representation corresponding to the second genetic variant identifier may be indicative of a difference between the first allele image representation and second allele image representation. A match and/or difference in the image region for the differential image representation may be indicated in a variety of ways including using numerical values, colors, and/or the like. For example, a match between image regions in the first image representation and second image representation may be indicated by an image region value of '1' and a non-match between image regions in the first image representation and second image representation may be indicated by an image region value of '0'.

As another example, a match between image regions in the first image representation and second image representation may be indicated by a white color in the corresponding image region while a non-match between image regions in the first image representation and second image representation may be indicated by a black color in the corresponding image region.

An operational example of an input feature 1300 that may be used to generate a differential image representation is depicted in FIG. 13. The input feature 1300 may comprise one or more feature values corresponding to one or more genetic variants 1302 for one or more individuals 1301. Based at least in part on these one or more feature values provided for the one or more individuals, a first allele value 1303 and a second allele value 1304 may be determined. For example, an individual with the feature values 'AG' for the genetic variant identifier rs1 may correspond to a value 'A' for the first allele value corresponding to the genetic variant identifier rs1 and a value 'G' for the second allele value corresponding to the genetic variant identifier rs1.

An operational example of one or more first allele or second allele image representations 1400-1403 that may be generated is depicted in FIGS. 14A-D. In this particular example, a DNA nucleotide input feature type designation is portrayed such that an image representation for each category associated with the DNA nucleotide input feature type designation is generated. In this case, each image representation corresponding to a category of the DNA nucleotide input feature type designation also corresponds to a unique color when indicating the presence of the corresponding feature value in the input feature for a particular image representation region. However, it will also be appreciated by one of skill in the art that each image representation from each category may be combined into a single image representation where each color uniquely represents a DNA nucleotide input feature type designation category. For example, a DNA nucleotide input feature type designation category of 'A' may correspond to a red color while a DNA nucleotide input feature type designation category of 'C' may correspond to a green color.

Once the first allele image representation and second allele image representation are generated, one or more mathematical and/or logical operators may be applied to generate a differential image representation. A match and/or difference in the image region for the differential image representation may be indicated in a variety of ways including using numerical values, colors, and/or the like. For example, a match between image regions in the first image representation and second image representation may be indicated by an image region value of '1' and a non-match between image regions in the first image representation and second image representation may be indicated by an image region value of '0'. As another example, a match between image regions in the first image representation and second image representation may be indicated by a white color in the corresponding image region while a non-match between image regions in the first image representation and second image representation may be indicated by a black color in the corresponding image region.

In some embodiments, step/operation 402 may be performed in accordance with the various steps/operations of the process 1500 that depicted in FIG. 15, which is a flowchart diagram of an example process for generating an intensity image representation.

The process 1500 depicted in FIG. 15 begins at step/operation 1501, when the feature extraction engine 111 identifies one or more initial image representations of the input feature. The one or more initial image representations may be generated by the process described in step/operation 402.

At step/operation 1502, the feature extraction engine 111 may assign one or more intensity values to each input feature type designation of the plurality of input feature type designations. In some embodiments, input feature type designations associated with feature values corresponding to a categorical feature type may have an intensity value assigned for each category of the input feature type designation. For example, a DNA nucleotide input feature type designation may be associated with categories 'A', 'C', 'T', 'G', and missing (corresponding to adenine, cytosine, thymine, and guanine, respectively) may be assigned intensity values 1, 0.75, 0.5, 0.25, and 0. Additionally or alternatively, the categories 'A', 'C', 'T', 'G', and missing may be assigned intensity values corresponding to the colors red, green, blue, white, and black, respectively. In some embodiments, input feature type designations associated with feature values corresponding to a numeric feature type may have an intensity value based at least in part on the numeric value of the feature value. For example, a MAF input feature type designation may be associated with a numeric value between 0 and 1. As such, a feature value of '0.3' for an MAF input feature type designation may be associated with an intensity value of 0.3. In some embodiments, intensity value for a feature value corresponding to a numeric input feature type may be rounded to the nearest integer or decimal place of interest. For example, a feature value of 0.312 for an MAF input feature type designation may be associated with an intensity value of 0.3.

At step/operation 1503, the feature extraction engine 111 may generate one or more intensity image representations of the one or more initial image representations. In some embodiments, the feature extraction engine 111 may generate the one or more intensity image representation based at least in part on the one or more feature values and the assigned intensity value for each input feature type designation.

In some embodiments, step/operation 402 may be performed in accordance with the various steps/operations of the process 1600 that depicted in FIG. 16, which is a flowchart diagram of an example process for generating a zygosity image representation.

The process 1600 depicted in FIG. 16 begins at step/operation 1601, when the feature extraction engine 111 generates a first allele image representation. In some embodiments, an input feature may describe a representation of a genetic sequence associated with an individual as indicated by feature values of an input feature associated with an individual. In some embodiments, the genetic sequence corresponds to one or more particular genes and/or alleles for a first chromosome and/or first set of chromosomes of the individual. The first allele image representation may be generated substantially similarly to the process described in step/operation 402.

At step/operation 1602, the feature extraction engine 111 generates a second allele image representation. In some embodiments, an input feature may describe a representation of a genetic sequence associated with an individual as indicated by feature values of an input feature associated with an individual. In some embodiments, the genetic sequence corresponds to one or more particular genes and/or alleles for a second chromosome and/or second set of chromosomes of the individual. In some embodiments, the individual associated with the second allele image is the same individual associated with the first allele image representation. In some embodiments, the individual associated with the second allele image is a different individual than the individual associated with the first allele image representation. The second allele image representation may be generated substantially similarly to the process described in step/operation 402.

At step/operation 1603, the feature extraction engine 111 generates a dominant allele image representation. In some embodiments, an input feature may describe a representation of a genetic sequence associated with a dominant genetic sequence for a particular genetic sequence as indicated by feature values of an input feature. In some embodiments, the genetic sequence corresponds to a particular gene and/or allele. In some embodiments, the dominant genetic sequence is the genetic sequence most common in a population. The dominant allele image representation may be generated substantially similarly to the process described in step/operation 402.

At step/operation 1604, the feature extraction engine 111 generates a minor allele image representation. In some embodiments, an input feature may describe a representation of a genetic sequence associated with a minor genetic sequence for a particular genetic sequence as indicated by feature values of an input feature. In some embodiments, the genetic sequence corresponds to a particular gene and/or allele. In some embodiments, the minor genetic sequence is the genetic sequence associated with a second most common genetic sequence in a population. In some embodiments, the minor genetic sequence is a genetic sequence associated other than the most common genetic sequence in a population. The minor allele image representation may be generated substantially similarly to the process described in step/operation 402.

At step/operation 1605, the feature extraction engine 111 generates a zygosity image representation. In some embodiments, a representation of a zygosity associated with an individual based at least in part on an associated first allele image representation and a second allele image representation for the individual, a dominant allele representation, and a minor allele representation for a genetic sequence (e.g. gene, allele, chromosome, etc.). In some embodiments, the zygosity image representation may be generated based at least in part on a comparison between the first allele image representation and a second allele image representation using one or more mathematical and/or logical operators, similar to the differential image representation. Further, the zygosity image representation may be generated based at least in part on a comparison between the between the first allele image representation, second allele image representation, dominant allele representation, and minor allele representation using one or more mathematical and/or logical operators. For example, if an individual is associated with a first allele image representation indicating a feature value of 'A' in the image region corresponding to the second genetic variant identifier and a second allele image representation indicates a feature value of 'C' in the image region corresponding to the second genetic variant identifier, the feature value for the second genetic variant identifier is determined to be heterozygous.

As another example, if an individual is associated with a first allele image representation indicating a feature value of 'A' in the image region corresponding to the first genetic variant identifier and a second allele image representation indicates a feature value of 'A' in the image region corresponding to the first genetic variant identifier, the feature value for the first genetic variant is determine to be homozygous. Further, the homozygous feature value of 'A' may be compared to the feature values corresponding to the first genetic variant identifier in the dominant allele image representation and/or minor allele image representation. If the homozygous feature value matches the feature value in the dominant allele image representation, the feature value is determined to be homozygous with a dominant allele. If the homozygous feature value matches the feature value in the minor allele image representation, the feature value is determined to be homozygous with a minor allele. A heterozygous, homozygous with a dominant allele, homozygous with a minor allele, etc. may be indicated in a variety of ways including using values corresponding to each category, colors corresponding to each category, etc. For example, an image region determined to be heterozygous may be associated with a value of '0', an image region determined to be homozygous with a dominant allele may be associated with a value of '1', and an image region determined to be homozygous with a dominant allele may be associated with a value of '2'.

As another example, an image region determined to be heterozygous may be associated with a green color, an image region determined to be homozygous with a dominant allele may be associated with a red color, and an image region determined to be homozygous with a dominant allele may be associated with a blue color.

An operational example of an input feature 1700 that may be used to generate a zygosity image representation is depicted in FIG. 17. The input feature 1700 may comprise one or more feature values for both the minor allele 1702 and dominant allele 1703 corresponding to one or more genetic variants 1701. Based at least in part on these one or more feature values provided by the input feature, a dominant allele value 1704 and a minor allele value 1705 may be determined.

An operational example of a first allele image representation, second allele image representation, dominant allele image representation, or minor allele image representation 1800 that may be used in part to generate a zygosity image representation is depicted in FIG. 18. By way example, a DNA nucleotide input feature type designation is portrayed. In this case, the image representation corresponding to a category of the DNA nucleotide input feature type designation also corresponds to a unique color when indicating the presence of the corresponding feature value in the input feature for a particular image representation region. For example, a DNA nucleotide input feature type designation category of 'A' may correspond to a red color, a DNA nucleotide input feature type designation category of 'C' may correspond to a green color, a DNA nucleotide input feature type designation category of 'G' may correspond to a blue color, a DNA nucleotide input feature type designation category of 'T' may correspond to a white color, and a DNA nucleotide input feature type designation category of 'missing' may correspond to a black color.

A zoomed in version of operational example depicted in FIG. 18 is depicted in FIG. 19. In FIG. 19, the individual colors each corresponding to an image representation region which further corresponds to a genetic variant identifier, is shown more clearly.

An operational example of a minor allele image representation 2001, dominant image representation 2002, first allele image representation 2003, second allele image representation 2004, and a zygosity image representation 2005 is depicted in FIG. 20. The feature extraction engine 111 may generate the zygosity image representation 2005 based at least in part on an associated first allele image representation and a second allele image representation for the individual, a dominant allele representation, and a minor allele representation for a genetic sequence (e.g. gene, allele, chromosome, etc.). In some embodiments, the zygosity image representation may be generated based at least in part on a comparison between the first allele image representation and a second allele image representation using one or more mathematical and/or logical operators, similar to the differential image representation. Further, the zygosity image representation may be generated based at least in part on a comparison between the between the first allele image representation, second allele image representation, dominant allele representation, and minor allele representation using one or more mathematical and/or logical operators.

Returning now to FIG. 4, at step/operation 403, the feature extraction engine 111 generates a tensor representation of the one or more image representations. In some embodiments, to generate the tensor representation, the feature extraction engine 111 retrieves configuration data for a particular image-based processing routine from the model definition data 121 stored in the storage subsystem 108. However, one of ordinary skill in the art will recognize that the feature extraction engine 111 may generate the one or more images by applying any suitable technique for transforming the input feature into the one or more images. In some embodiments, the feature extraction engine 111 selects a suitable image-based processing routine for the tensor representation given the one or more properties of the input feature (e.g., inclusion of input feature type designations for the input feature, an indication of feature values pertaining to one or more individuals, and/or the like). In some embodiments, the feature extraction engine 111 may select a suitable image-based processing routine for the input feature based at least in part on a user specified preference. In some embodiments, the user specified preference may be indicated in the input feature.

An operational example of generating a tensor representation 900 of the one or more image representations is depicted in FIG. 9. Each image representation 901 in the tensor representation 900 corresponds to an image representation generated by the feature extraction engine 111. By way of continuing example, the tensor representation 900 may comprise 4 image representations corresponding to the DNA Nucleotide input feature type designation and 1 image representation corresponding to the MAF input feature type designation.

At step/operation 404, the feature extraction engine 111 generates a plurality of positional encoding maps. In some embodiments, to generate the positional encoding maps, the feature extraction engine 111 retrieves configuration data for a particular image-based processing routine from the model definition data 121 stored in the storage subsystem 108. However, one of ordinary skill in the art will recognize that the feature extraction engine 111 may generate the plurality of positional encoding maps by applying any suitable technique for generating a plurality of positional encoding maps. In some embodiments, the feature extraction engine 111 selects a suitable image-based processing routine for the plurality of positional encoding maps given the one or more properties of the input feature (e.g., inclusion of input feature type designations for the input feature, an indication of feature values pertaining to one or more individuals, and/or the like). In some embodiments, the feature extraction engine 111 may select a suitable image-based processing routine for the plurality of positional encoding maps based at least in part on a user specified preference. In some embodiments, once the plurality of positional encoding maps are generated, they may be incorporated into the tensor representation A positional encoding map may be comprised of positional encoding map regions each corresponding to a genetic variant identifier. Each region of a positional encoding map may correspond to an identifier value. For example, the first positional encoding map region may comprise an identifier value of '1', the second positional encoding map region may comprise an identifier value of '2', etc. In some embodiments, a positional encoding map set may comprise each positional encoding map region corresponding to the same genetic variant identifier across the plurality of positional encoding maps. For example, if the plurality of positional encoding maps comprise two positional encoding maps, and the positional encoding map regions corresponding to the first genetic variant identifier in both positional encoding maps comprise an identifier value of '1', the positional encoding map region set for the first genetic variant identifier may comprise the identifier values '1,1'. In some embodiments, the identifier values of the positional encoding map corresponding to each positional encoding map regions are the same. In some embodiments, the identifier values of the positional encoding map corresponding to each positional encoding map regions are the different.

An operational example of generating a plurality of positional encoding maps 1000 is depicted in FIG. 10. In this particular example, the plurality of positional encoding maps 1000 comprises two positional encoding maps 1000a and 1000b. Each positional encoding map comprises a plurality of positional encoding map regions 1001-1009 for positional encoding map 1000a and 1010-1018 for positional encoding map 1000b. Each positional encoding map region corresponds to a genetic variant identifier. In some embodiments, the number of positional encoding map regions is based at least in part on the image representation configuration as described with reference to FIG. 6. The value for each positional encoding map region may be assigned an identifier value. An identifier value may be any value such as a numeric value, color, symbols, etc. For example, positional encoding map 1000a has 9 positional encoding map regions comprising the values 1-9, respectively. Similarly, positional encoding map 1000b has 9 positional encoding map regions comprising the values 1-9, respectively.

In some embodiments, one or more positional encoding map regions may comprise the same value. For example, positional encoding map 1000c includes positional encoding map regions 1019, 1022, and 1025, which are assigned the same identifier value. Similarly, positional encoding map 1000d includes positional encoding map regions 1028, 1029, and 1030, which are assigned the same identifier value.

A positional encoding map region set is comprised of each positional encoding map region from amongst the plurality of positional encoding maps corresponding to the same genetic variant identifier. For example, a positional encoding map region set for the genetic variant identifier rs1 may comprise the positional encoding map regions 1001 and 1010 from positional encoding map 1000a and 1000b, respectively. As such, the positional encoding map region set may correspond to '1,1'. As such, the genetic variant identifier rs1 may be assigned the positional encoding map region set corresponding to '1,1' such that no other genetic variant identifier is assigned the positional encoding map region set. As another example, the positional encoding map region set for the genetic variant identifier rs2 may comprise the positional encoding map regions 1002 and 1012 from positional encoding map 1000a and 1000b, respectively. As such, the positional encoding map region set may correspond to '2,2'. As such, the genetic variant identifier rs2 may be assigned the positional encoding map region set corresponding to '2,2'. As another example, a positional encoding map region set for the genetic variant identifier rs1 may comprise the positional encoding map regions 1019 and 1028 from positional encoding map 1000c and 1000d, respectively. As such, the positional encoding map region set may correspond to '1,1'. As such, the genetic variant identifier rs1 may be assigned the positional encoding map region set corresponding to '1,1' such that no other genetic variant identifier is assigned the positional encoding map region set. As another example, the positional encoding map region set for the genetic variant identifier rs2 may comprise the positional encoding map regions 1020 and 1029 from positional encoding map 1000c and 1000d, respectively. Accordingly, the positional encoding map region set may correspond to '2,1'. As such, the genetic variant identifier rs2 may be assigned the positional encoding map region set corresponding to '2,1'.

Another operational example of generating a plurality of positional encoding maps 2100 is also depicted in FIG. 21. In this particular example, the plurality of positional encoding maps 2100 comprises two positional encoding maps 2100a and 2100b. The positional encoding map region set is comprised on a unique set of intensity values from which a genetic variant identifier may be identified.

An operational example of incorporating the plurality of positional encoding maps into the tensor representation 1100 is depicted in FIG. 11. The tensor representation comprising the one or more generated image representations 1102 may additionally incorporate the plurality of positional encoding maps 1101. In some embodiments, the plurality of positional encoding maps may uniquely identify a particular genetic variant identifier present in the one or more image representations 1102.

Another operational example of incorporating the plurality of positional encoding maps into the tensor representation 2200 is depicted in FIG. 22. The tensor representation comprising the one or more generated image representations 2202-2205 may additionally incorporate the plurality of positional encoding maps 2201. In some embodiments, the plurality of positional encoding maps may uniquely identify a particular genetic variant identifier present in the one or more image representations 1102. In this example, the tensor representation includes one or more image representations for a second allele image representation 2202, one or more image representations for a first allele image representation 2203, one or more image representations for a dominant allele image representation 2204, one or more image representations a minor allele image representation 2205, and plurality of positional encoding maps 2201.

Returning now to FIG. 4, at step/operation 405, the predictive analysis engine 112 processes the one or images using an image-based machine learning model to generate one or more predictions. Examples of an image-based machine learning models include a machine learning model that utilizes a convolutional neural network (CNN). Other examples of an image-based machine learning model include a feedforward neural network. In some embodiments, the image-based machine learning model may utilize a CNN in coordination with one or more other machine learning models.

In some embodiments, step/operation 403 may be performed in accordance with the CNN architecture 2300 depicted in the block diagram of FIG. 23. As depicted in FIG. 23, the predictive analysis engine 112 receives one or more images 2301 generated by the feature extraction engine 111 using one or more input layers 2302. As further depicted in FIG. 23, the predictive analysis engine 112 utilizes one or more feature learning layers 2303 to process the output of the one or more input layers 2302 to generate one or more convolutional layer outputs. In some embodiments, the one or more feature learning layers 2303 are configured to perform a combination of one or more successive feature learning routines, where each feature learning routine of the one or more successive feature routines includes performing a convolutional operation (e.g., a convolutional operation using one or more kernels and/or one or more filters) followed by an activation operation (e.g., a rectified linear unit (ReLU) activation operation) and followed by a pooling operation (e.g., a non-linear down-sampling operation, such as a max pool operation). For example, as depicted in the block diagram of FIG. 24, the one or more feature learning layers 2303 may include two successive feature learning routines, i.e., a first convolutional operation performed by a first convolutional layer 2401, followed by a first activation operation by a first activation layer 2402, followed by a first pooling operation by a first pooling layer 2403, followed by a second convolutional operation by a second convolutional layer 2404, followed by a second activation operation by a second activation layer 2405, and followed by a second pooling operation by a second pooling layer 2406.

As further depicted in FIG. 23, the predictive analysis engine 112 utilizes one or more prediction layers 2304 to process the one or more convolutional layer outputs generated by the one or more feature learning layers 2303 to generate one or more raw prediction outputs. In some embodiments, the one or more prediction layers 2304 including one or more fully connected neural network layers. For example, as depicted in the block diagram of FIG. 25, the one or more prediction layers 2304 may include a flattening layer 2501 configured to generate a flattened version of the one or more convolutional layer outputs generated by the one or more feature learning layers 2303, two fully connected layers 2502-2503, and a normalization layer 2504 (e.g., a SoftMax normalization layer). Moreover, the predictive analysis engine 112 utilizes one or more output layers 2305 to generate one or more predictions 2306 based at least in part on the raw prediction outputs generated by the one or more prediction layers 2304.

At step/operation 406, the predictive analysis engine 112 performs a prediction-based action based at least in part on the predictions generated in step/operation 405. Examples of prediction-based actions include transmission of communications, activation of alerts, automatic scheduling of appointments, and/or the like. As a further example, the predictive analysis engine 112 may determine a polygenic risk score (PRS) for one or more diseases for one or more individuals based at least in part on the predictions generated in step/operation 405.

Using the above-described techniques, various embodiments of the present invention address technical challenges related to efficiently and reliably performing predictive data analysis in prediction domains. For example, in some embodiments, proposed solutions disclose generating one or more image representations of an input feature comprising one or more feature values each corresponding to a genetic variant identifier and associated with an input feature type designation. Each image representation may comprise a plurality of image regions which correspond to a genetic variant identifier. The image representations may be further processed to generate a differential image representation, zygosity image representation, and intensity image representation. In some embodiments, a tensor representation of the one or more image representations is generated. Further in some embodiments, a plurality of positional encoding maps are generated and each genetic variant identifier is associated with a positional encoding map region set comprising each positional encoding map region associated with the genetic variant identifier across the plurality of positional encoding maps and are also included in the tensor representation. After generation, the tensor representation of the various image representations and/or positional encoding maps can be utilized by an image-based machine learning model (e.g., a machine learning model utilizing a CNN) to perform efficient and reliable predictive data analysis. The resulting machine learning solutions are more efficient to train and more reliable when trained. In doing so, various embodiments of the present invention address shortcomings of existing predictive data analysis solutions and enable solutions that are capable of efficiently and reliably performing predictive data analysis in prediction domains with complex input spaces.

Many existing predictive data analysis solutions are incapable of efficiently and reliably performing predictive data analysis in prediction domains with complex input spaces. This is because many existing predictive data analysis solutions are developed for more common predictive data analysis tasks like image classification. For example, in the image classification domain, convolution neural networks (CNNs) have achieved tremendous success in efficiently and accurately performing predictive data analysis. Such solutions, however, are largely out of reach of developers in prediction domains with more complex input structures, such as prediction domains with high-dimensional categorical feature spaces. Thus, there is a technical need for predictive data analysis solutions that are capable of efficiently and reliably performing predictive data analysis in prediction domains with complex input spaces.

To address the above-noted need, various embodiments of the present invention address technical challenges related to efficiently and reliably performing predictive data analysis in complex prediction domains. For example, in some embodiments, proposed solutions disclose generating one or more image representations of an input feature comprising one or more feature values each corresponding to a genetic variant identifier and associated with an input feature type designation. Each image representation may comprise a plurality of image regions which correspond to a genetic variant identifier. The image representations may be further processed to generate a differential image representation, zygosity image representation, and intensity image representation. In some embodiments, a tensor representation of the one or more image representations is generated. Further in some embodiments, a plurality of positional encoding maps are generated and each genetic variant identifier is associated with a positional encoding map region set comprising each positional encoding map region associated with the genetic variant identifier across the plurality of positional encoding maps and are also included in the tensor representation. After generation, the tensor representation of the various image representations and/or positional encoding maps can be utilized by an image-based machine learning model (e.g., a machine learning model utilizing a CNN) to perform efficient and reliable predictive data analysis. The resulting machine learning solutions are more efficient to train and more reliable when trained. In doing so, various embodiments of the present invention address shortcomings of existing predictive data analysis solutions and enable solutions that are capable of efficiently and reliably performing predictive data analysis in prediction domains with complex input spaces.

Training Image-Based Prediction Models

FIG. 26 is a flowchart diagram of an example process 2600 for training a machine learning model for performing image-based predictive data analysis. Via the various steps/operations of the process 2600, the predictive data analysis computing entity 106 can train a machine learning model to process categorical input features (e.g., structured text input features) to generate one or more predictive data analysis conclusions.

The process 2600 begins at step/operation 2601 when the feature extraction engine 111 obtains/receives one or more training data objects, where each training data object includes one or more training input features and one or more ground-truth determinations for the one or more input features. For example, the one or more training input features in a particular training data object may include one or more patient features for a patient, while the one or more ground-truth determinations in the particular training data object may include particular health information (e.g., particular diagnostic information) associated with the patient predictive entity. As another example, the one or more training categorical input features in a particular training data object may include one or more operational features for a medical provider predictive entity, while the one or more ground-truth determinations in the particular training data object may include particular operational information (e.g., particular operational statistics) associated with the medical provider predictive entity. The feature extraction engine 111 may retrieve the categorical input features from the training data 122 stored on the storage subsystem and/or receive the categorical input features from the training data 122 from one or more external computing entities 102.

At step/operation 2602, the feature extraction engine 111 generates one or more images based at least in part on the one or more training data objects obtained/received in step/operation 2601. For example, the feature extraction engine 111 may process the one or more categorical training input features associated with the training data objects (e.g., in accordance with a process substantially similar to the process 400 of FIG. 4) to generate one or more images based at least in part on the one or more training data objects obtained/received in step/operation 2601. In some embodiments, the feature extraction engine 111 provides the generated one or more images to the predictive analysis engine 112.

At step/operation 2603, the predictive analysis engine 112 generates one or more predictions based at least in part on the one or more images generated in step/operation 2604. For example, the predictive analysis engine 112 may process the one or more images generated by the predictive analysis engine 112 (e.g., using a CNN, such as the CNN architecture 2300 of FIG. 23) to generate one or more predictions based at least in part on the one or more images generated by the feature extraction engine 111 in step/operation 2602. In some embodiments, the predictive analysis engine 112 provides the generated one or more predictions to the training engine 113. At step/operation 2604, the training engine 113 generates an error model based at least in part on the one or more predictions. In some embodiments, the training engine 113 generates a measure of deviation between each of the one or more predictions and a corresponding ground-truth determination in a training data object associated with the particular prediction. The training engine 113 may then compute an overall error measure based at least in part on the measure of deviation. The training engine 113 may then generate the error model as a model that relates the overall error measure to one or more trainable parameters of the machine learning model (e.g., at least one of one or more trainable parameters associated with the feature extraction engine 111 and one or more trainable parameters associated with the predictive analysis engine 112). At step/operation 2605, the training engine 113 generates updated values for one or more trainable parameters of the machine learning model in a manner that achieves an optimization of the error model. In some embodiments, the training engine 113 may generate the updated values for the one or more trainable parameters of the machine learning model in a manner that achieves a local optimization of the error model. In some embodiments, the training engine 113 may generate the updated values for the one or more trainable parameters of the machine learning model in a manner that achieves a global optimization of the error model. In some embodiments, to generate the updated values for the one or more trainable parameters of the machine learning model in a manner that achieves an optimization of the error model, the training engine 113 uses one or more training algorithms, such as a gradient-descent-based training algorithm.

Although the techniques described herein for generating image representations of categorical feature data are explained with reference to performing predictive data analysis, a person of ordinary skill in the relevant technology will recognize that the disclosed techniques have applications far beyond performing predictive data analysis. As an illustrative example, the disclosed techniques can be used in various data visualization applications. As another illustrative example, the disclosed techniques can be used to encode data in image-based data structures that facilitate at least one of data retrieval and data security. As yet another example, the disclosed techniques can be utilized to enhance various steganography techniques. As a further illustrative example, the disclosed techniques can be used to process and store data in spatial-temporal databases. In some embodiments, the disclosed techniques can be used to generate video representations of categorical feature data, e.g., video representations that illustrate changes in the corresponding categorical feature over time.

Other Predictive Data Analysis Operations

In some embodiments, a machine learning model may be configured to process a set of image representations and a positional encoding map for each image representation that describes positional occurrences of particular features (e.g., genetic variants) in the image representation to generate one or more desired outputs (e.g., one or more polygenic risk scores (PRSs) for one or more target conditions). For example, the set of image representations may include an image representation corresponding to a genome-wide association study (GAWS) statistics map and/or an image representation corresponding to a map of risk allele counts. In some embodiments, a machine learning model (e.g., a CNN model) may be configured to process the set of image representations containing genetic information of a target individual in order to generate one or more target PRS scores for the individual.

In some embodiments, a machine learning model may be configured to process genotypic data for (e.g., an average of all tensor representations of genetic sequences of) a set of individuals that are deemed to have a particular condition, genotypic data for (e.g., an average of all tensor representations of genetic sequences of) a set of individuals that are deemed to not have a particular condition, and genotypic data for (e.g., the tensor representation of the genetic sequence of) a target individual to determine a risk score (e.g., a PRS) for the target individual with respect to the target condition. In some embodiments, the machine learning model is an image-based machine learning model, such as a CNN. In some embodiments, the genotypic data having image forms, while in other embodiments they have other forms (e.g., text forms).

Thus, as described above, various embodiments of the present invention address technical challenges related to efficiently and reliably performing predictive data analysis in prediction domains. For example, in some embodiments, proposed solutions disclose generating one or more image representations of an input feature comprising one or more feature values each corresponding to a genetic variant identifier and associated with an input feature type designation. Each image representation may comprise a plurality of image regions which correspond to a genetic variant identifier. The image representations may be further processed to generate a differential image representation, zygosity image representation, and intensity image representation. In some embodiments, a tensor representation of the one or more image representations is generated. Further in some embodiments, a plurality of positional encoding maps are generated and each genetic variant identifier is associated with a positional encoding map region set comprising each positional encoding map region associated with the genetic variant identifier across the plurality of positional encoding maps and are also included in the tensor representation. After generation, the tensor representation of the various image representations and/or positional encoding maps can be utilized by an image-based machine learning model (e.g., a machine learning model utilizing a CNN) to perform efficient and reliable predictive data analysis. The resulting machine learning solutions are more efficient to train and more reliable when trained. In doing so, various embodiments of the present invention address shortcomings of existing predictive data analysis solutions and enable solutions that are capable of efficiently and reliably performing predictive data analysis in prediction domains with complex input spaces.

VI. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method for dynamically generating an image-based prediction, the computer-implemented method comprising:
    receiving, by one or more processors, an input feature, wherein the input feature comprises one or more feature values, wherein each feature value of the one or more feature values corresponds to a genetic variant identifier of a plurality of genetic variant identifiers, and wherein each feature value of the one or more feature values is associated with an input feature type designation of a plurality of input feature type designations;
    generating, by the one or more processors, one or more image representations of the input feature, wherein: (i) an image representation count of the one or more image representations of the input feature is based at least in part on the plurality of input feature type designations (ii) each image representation of the one or more image representations of the input feature comprises a plurality of image regions, (iii) each image region of the plurality of image regions for an image representation of the one or more image representations of the input feature corresponds to a genetic variant identifier of the plurality of genetic variant identifiers, and (iv) generating each of the one or more image representations of the input feature associated with a character category is performed based at least in part on the one or more feature values of the input feature having the input feature type designation;
    generating, by the one or more processors, a tensor representation of the one or more image representations of the input feature;
    generating, by the one or more processors, one or more positional encoding maps, wherein: (i) each positional encoding map of the one or more positional encoding maps comprises a plurality of positional encoding map regions, (ii) each positional encoding map region of the plurality of positional encoding map regions for a positional encoding map corresponds to a genetic variant identifier of the plurality of genetic variant identifiers, (iii) each specific genetic variant identifier of the plurality of genetic variant identifiers is associated with a positional encoding map region set, of one or more positional encoding map region sets, comprising each positional encoding map region of the plurality of positional encoding map regions associated with the specific genetic variant identifier across the one or more positional encoding maps, and (iv) each positional encoding map region set of the one or more positional encoding map region sets for a particular genetic variant identifier of the plurality of genetic variant identifiers represents the particular genetic variant identifier;
    generating, by the one or more processors, the image-based prediction based at least in part on the tensor representation of the one or more image representations of the input feature and the one or more positional encoding maps; and
    performing, by the one or more processors, one or more prediction-based actions based at least in part on the image-based prediction.

2. The computer-implemented method of claim 1, wherein generating the one or more image representations of the input feature further comprises:
    generating, by the one or more processors, a first image representation generated based at least in part on a first subset of input features;
    generating, by the one or more processors, a second image representation generated based at least in part on a second subset of input features; and
    generating, by the one or more processors, a differential image representation of the one or more image representations of the input feature based at least in part on performing an image difference operation across the first image representation and the second image representation.

3. The computer-implemented method of claim 1, wherein generating the one or more image representations of the input feature further comprises:
    generating, by the one or more processors, a first allele image representation generated based at least in part on a first subset of input features corresponding to a first allele;
    generating, by the one or more processors, a second allele image representation generated based at least in part on a second subset of input features corresponding to a second allele;
    generating, by the one or more processors, a dominant allele image representation generated based at least in part on a dominant subset of input features corresponding to a dominant allele;
    generating, by the one or more processors, a minor allele image representation generated based at least in part on a minor subset of input features corresponding to a minor allele; and
    generating, by the one or more processors, a zygosity image representation of the one or more image representations of the input feature based at least in part on performing one or more operations across the first allele image representation, the second allele image representation, the dominant allele image representation, and the minor allele image representation.

4. The computer-implemented method of claim 1, wherein generating the one or more image representations of the input feature further comprises:
    identifying one or more initial image representations of the input feature;
    assigning, by the one or more processors, one or more intensity values to each input feature type designation of the plurality of input feature type designations;
    generating, by the one or more processors, one or more intensity image representations of the one or more initial image representations, wherein (i) each image representation of the one or more intensity image representations comprises a plurality of intensity image regions, (ii) each image region of the plurality of intensity image regions for an intensity image representation corresponds to a genetic variant identifier of the plurality of genetic variant identifiers, and (iii) generating the one or more intensity image representations is determined based at least in part on the one or more feature values and the one or more assigned intensity value for each input feature type designation of the plurality of input feature type designations.

5. The computer-implemented method of claim 1, wherein the image-based prediction comprises generating, by the one or more processors, a polygenic risk score for one or more diseases for one or more individuals associated with the input feature.

6. The computer-implemented method of claim 1, wherein each feature value of the one or more feature values corresponds to a categorical feature type or numerical feature type.

7. The computer-implemented method of claim 1, wherein each feature value of the one or more feature values further corresponds to a chromosome number and locus.

8. A system for dynamically generating an image-based prediction, the system comprising one or more processors and memory including program code, the memory and the program code configured to, with the one or more processors, cause the system to at least:
receive an input feature, wherein the input feature comprises one or more feature values, wherein each feature value of the one or more feature values corresponds to a genetic variant identifier of a plurality of genetic variant identifiers, and wherein each feature value of the one or more feature values is associated with an input feature type designation of a plurality of input feature type designations;
generate one or more image representations of the input feature, wherein: (i) an image representation count of the one or more image representations of the input feature is based at least in part on the plurality of input feature type designations (ii) each image representation of the one or more image representations of the input feature comprises a plurality of image regions, (iii) each image region of the plurality of image regions for an image representation of the one or more image representations of the input feature corresponds to a genetic variant identifier of the plurality of genetic variant identifiers, and (iv) generating each of the one or more image representations of the input feature associated with a character category is performed based at least in part on the one or more feature values of the input feature having the input feature type designation;
generate a tensor representation of the one or more image representations of the input feature;
generate one or more positional encoding maps, wherein: (i) each positional encoding map of the one or more positional encoding maps comprises a plurality of positional encoding map regions, (ii) each positional encoding map region of the plurality of positional encoding map regions for a positional encoding map corresponds to a genetic variant identifier of the plurality of genetic variant identifiers, (iii) each specific genetic variant identifier of the plurality of genetic variant identifiers is associated with a positional encoding map region set, of one or more positional encoding map region sets, comprising each positional encoding map region of the plurality of positional encoding map regions associated with the specific genetic variant identifier across the one or more positional encoding maps, and (iv) each positional encoding map region set of the one or more positional encoding map region sets for a particular genetic variant identifier of the plurality of genetic variant identifiers represents the particular genetic variant identifier;
generate the image-based prediction based at least in part on the tensor representation of the one or more image representations of the input feature and the one or more positional encoding maps; and
perform one or more prediction-based actions based at least in part on the image-based prediction.

9. The system of claim 8, the memory and the program code are further configured to, with the one or more processors, cause the system to:
generate a first image representation generated based at least in part on a first subset of input features;
generate a second image representation generated based at least in part on a second subset of input features; and
generate a differential image representation of the one or more image representations of the input feature based at least in part on performing an image difference operation across the first image representation and the second image representation.

10. The system of claim 8, the memory and the program code are further configured to, with the one or more processors, cause the system to:
generate a first allele image representation generated based at least in part on a first subset of input features corresponding to a first allele;
generate a second allele image representation generated based at least in part on a second subset of input features corresponding to a second allele;
generate a dominant allele image representation generated based at least in part on a dominant subset of input features corresponding to a dominant allele;
generate a minor allele image representation generated based at least in part on a minor subset of input features corresponding to a minor allele;
generate a zygosity image representation of the one or more image representations of the input feature based at least in part on performing one or more operations across the first allele image representation, the second allele image representation, the dominant allele image representation, and the minor allele image representation.

11. The system of claim 8, the memory and the program code are further configured to, with the one or more processors, cause the system to:
identify one or more initial image representations of the input feature;
assign one or more intensity values to each input feature type designation of the plurality of input feature type designations;
generate one or more intensity image representations of the one or more initial image representations, wherein (i) each image representation of the one or more intensity image representations comprises a plurality of intensity image regions, (ii) each image region of the plurality of intensity image regions for an intensity image representation corresponds to a genetic variant identifier of the plurality of genetic variant identifiers, and (iii) generating the one or more intensity image representations is determined based at least in part on the one or more feature values and the one or more assigned intensity value for each input feature type designation of the plurality of input feature type designations.

12. The system of claim 8, wherein to generate the image-based prediction, the memory and the program code are further configured to, with the one or more processors, cause the system to generate a polygenic risk score for one or more diseases for one or more individuals associated with the input feature.

13. The system of claim 8, wherein each feature value of the one or more feature values corresponds to a categorical feature type or numerical feature type.

14. The system of claim 8, wherein each feature value of the one or more feature values further corresponds to a chromosome number and locus.

15. A computer program product for dynamically generating an image-based prediction, the computer program product comprising at least one non-transitory computer-readable storage medium having computer-readable program code portions stored therein, the computer-readable program code portions configured to:
   receive an input feature, wherein the input feature comprises one or more feature values, wherein each feature value of the one or more feature values corresponds to a genetic variant identifier of a plurality of genetic variant identifiers, and wherein each feature value of the one or more feature values is associated with an input feature type designation of a plurality of input feature type designations;
   generate one or more image representations of the input feature, wherein: (i) an image representation count of the one or more image representations of the input feature is based at least in part on the plurality of input feature type designations (ii) each image representation of the one or more image representations of the input feature comprises a plurality of image regions, (iii) each image region of the plurality of image regions for an image representation of the one or more image representations of the input feature corresponds to a genetic variant identifier of the plurality of genetic variant identifiers, and (iv) generating each of the one or more image representations of the input feature associated with a character category is performed based at least in part on the one or more feature values of the input feature having the input feature type designation;
   generate a tensor representation of the one or more image representations of the input feature;
   generate one or more positional encoding maps, wherein: (i) each positional encoding map of the one or more positional encoding maps comprises a plurality of positional encoding map regions, (ii) each positional encoding map region of the plurality of positional encoding map regions for a positional encoding map corresponds to a genetic variant identifier of the plurality of genetic variant identifiers, (iii) each specific genetic variant identifier of the plurality of genetic variant identifiers is associated with a positional encoding map region set, of one or more positional encoding map region sets, comprising each positional encoding map region of the plurality of positional encoding map regions associated with the specific genetic variant identifier across the one or more positional encoding maps, and (iv) each positional encoding map region set of the one or more positional encoding map region sets for a particular genetic variant identifier of the plurality of genetic variant identifiers represents the particular genetic variant identifier;
   generate the image-based prediction based at least in part on the tensor representation of the one or more image representations of the input feature and the one or more positional encoding maps; and
   perform one or more prediction-based actions based at least in part on the image-based prediction.

16. The computer program product of claim 15, wherein the computer-readable program code portions is further configured to:
   generate a first image representation generated based at least in part on a first subset of input features;
   generate a second image representation generated based at least in part on a second subset of input features; and
   generate a differential image representation of the one or more image representations of the input feature based at least in part on performing an image difference operation across the first image representation and the second image representation.

17. The computer program product of claim 15, wherein the computer-readable program code portions is further configured to:
   generate a first allele image representation generated based at least in part on a first subset of input features corresponding to a first allele;
   generate a second allele image representation generated based at least in part on a second subset of input features corresponding to a second allele;
   generate a dominant allele image representation generated based at least in part on a dominant subset of input features corresponding to a dominant allele;
   generate a minor allele image representation generated based at least in part on a minor subset of input features corresponding to a minor allele;
   generate a zygosity image representation of the one or more image representations of the input feature based at least in part on performing one or more operations across the first allele image representation, the second allele image representation, the dominant allele image representation, and the minor allele image representation.

18. The computer program product of claim 15, wherein the computer-readable program code portions is further configured to:
   identify one or more initial image representations of the input feature;
   assign one or more intensity values to each input feature type designation of the plurality of input feature type designations;
   generate one or more intensity image representations of the one or more initial image representations, wherein (i) each image representation of the one or more intensity image representations comprises a plurality of intensity image regions, (ii) each image region of the plurality of intensity image regions for an intensity image representation corresponds to a genetic variant identifier of the plurality of genetic variant identifiers, and (iii) generating the one or more intensity image representations is determined based at least in part on the one or more feature values and the one or more assigned intensity value for each input feature type designation of the plurality of input feature type designations.

19. The computer program product of claim 15, wherein the image-based prediction comprises generating a polygenic risk score for one or more diseases for one or more individuals associated with the input feature.

20. The computer program product of claim 15, wherein each feature value of the one or more feature values corresponds to a categorical feature type or numerical feature type.

* * * * *